(12) United States Patent
Kennedy et al.

(10) Patent No.: US 7,468,358 B2
(45) Date of Patent: Dec. 23, 2008

(54) METHOD AND MEDICAMENT FOR SULFATED POLYSACCHARIDE TREATMENT OF HEPARIN-INDUCED THROMBOCYTOPENIA (HIT) SYNDROME

(75) Inventors: Thomas Preston Kennedy, Charlotte, NC (US); Jeanine M. Walenga, Lombard, IL (US)

(73) Assignee: Paringenix, Inc., Tucson, AZ (US)

( * ) Notice: Subject to any disclaimer, the term of this patent is extended or adjusted under 35 U.S.C. 154(b) by 448 days.

(21) Appl. No.: 10/974,566

(22) Filed: Oct. 27, 2004

(65) Prior Publication Data

US 2007/0123489 A1 May 31, 2007

Related U.S. Application Data

(63) Continuation of application No. 10/869,370, filed on Jun. 16, 2004, now abandoned.

(51) Int. Cl.
*A61K 31/727* (2006.01)
*C08B 37/10* (2006.01)

(52) U.S. Cl. .......................................... 514/56; 536/21
(58) Field of Classification Search ........................ None
See application file for complete search history.

(56) References Cited

U.S. PATENT DOCUMENTS

| 5,668,118 | A | 9/1997 | Kennedy et al. | |
|---|---|---|---|---|
| 5,707,974 | A | 1/1998 | Kennedy | |
| 5,912,237 | A | 6/1999 | Kennedy | |
| 5,990,097 | A | * 11/1999 | Kennedy | 514/56 |
| 6,077,683 | A | 6/2000 | Kennedy | |
| 6,489,311 | B1 | 12/2002 | Kennedy et al. | |
| 6,743,426 | B2 | 6/2004 | Fisher et al. | |
| 2005/0261241 | A1* | 11/2005 | Cardin | 514/54 |
| 2005/0282775 | A1* | 12/2005 | Kennedy | 514/56 |

FOREIGN PATENT DOCUMENTS

| WO | WO98/04133 A | 2/1998 |
|---|---|---|
| WO | WO01/19376 A | 3/2001 |
| WO | WO 01/82918 | 11/2001 |
| WO | WO 2004/050673 A2 | 6/2004 |
| WO | WO 2006/007392 A1 | 1/2006 |

OTHER PUBLICATIONS

Walenga et al., "Heparin-induced thrombocytopenia, paradoxical thromboembolism, and other adverse effects of heparin-type therapy", *Hematology/Oncology Clinics of North America*, 2003, pp. 259-282, vol. 17.
Messmore et al., "Benefit-Risk Assessment of Treatments for Heparin-Induced Thrombocytopenia", *Drug Safety 2003*, 2003, pp. 625-641.
Fabris et al., "Pathophysiology of Heparin-Induced Thrombocytopenia", *Arch Pathol Lab Med*, Nov. 2000, pp. 1657-1666, vol. 124.
Walenga et al., "Mechanisms of Venous and Arterial Thrombosis in Heparin-Induced Thrombocytopenia", *Journal of Thrombosis and Thrombolysis*, 2000, pp. S13-S20.
Walenga et al., "Vascular Damage Correlates Between Heparin-Induced Thrombocytopenia and the Antiphospholipid Syndrome", *Clin Appl Thrombosis/Hemostasis*, 1999, pp. S76-S84, vol. 5.
Walenga et al., "Newer Insights on the Mechanism of Heparin-Induced Thrombocytopenia", *Seminars in Thrombosis and Hemostatis*, 2004, pp. 57-67, vol. 30, Supplement 1.
Walenga et al., "Relative Heparin-Induced Thrombocytopenic Potential of Low Molecular Weight Heparins and New Antithrombotic Agents", *Clin Appl Thrombosis/Hemostasis*, 1996, pp. S21-S27, vol. 2.
Haas et al., "Heparin-induced Thrombocytopenia: Clinical Considerations of Alternative Anticoagulation with Various Glycosaminoglycans and Thrombin Inhibitors", *Clin Appl Thrombosis/Hemostasis*, 1999, pp. 52-59, vol. 5.
Jeske et al., "Heparin-Induced Thrombocytopenic Potential of GAG and Non-GAG-Based Antithrombotic Agents", *Clin Appl Thrombosis/Hemostasis*, 1999, pp. S56-S62, vol. 5.
Walenga et al., "Biochemical and Pharmacologic Rationale for the Development of a Synthetic Heparin Pentasaccharide", *Thrombosis Research*, 1997, pp. 1-36, vol. 86, No. 1.
Walenga et al., "Fondaparinux: a synthetic heparin pentasaccharide as a new antithrombotic agent", *Expert Opin. Investig. Drugs*, 2002, pp. 397-407, vol. 11.
Ahmad et al., "Synthetic Pentasaccharides Do Not Cause Platelet Activation by Antiheparin-Platelet Factor 4 Antibodies", *Clin Appl Thrombosis/Hemostasis*, 1999, pp. 259-266, vol. 5.
Walenga et al., "Decreased Prevalence of Heparin-Induced Thrombocytopenia with Low-Molecular-Weight Heparin and Related Drugs", *Seminars in Thrombosis and Hemostasis*, 2004, pp. 69-80,, vol. 30, supplement 1.
Ahmad, S., et al., "Functional Heterogeneity of Antiheparin-Platelet Factor 4 Antibodies: Implications in the Pathogenesis of the HIT Syndrome," *Clinical and Applied Thrombosis/Hemostatis: Official Journal of the International Academy of Clinical and Applied Thrombosis/Hemostatis*, 1999, pp. S32-S37, vol. 5(1).
Fryer A. et al., "Selective O-desulfation produces nonanticoagulant heparin that retains pharmacological activity in the lung", *The Journal of Pharmacology and Experimental Therapeutics*, vol. 282, No. 1, Jul. 1997 pp. 208-219.

(Continued)

*Primary Examiner*—Shaojia Anna Jiang
*Assistant Examiner*—Eric S Olson
(74) *Attorney, Agent, or Firm*—Alston & Bird LLP

(57) ABSTRACT

A method and medicament for treating and preventing platelet activation or thrombosis in the presence of heparin-and platelet factor 4-complex reactive antibodies using a 2-O desulfated heparin with an average degree of sulfation of 0.6 sulfate groups per monosaccharide or greater and an average molecular weight or 2.4 kD or greater. The medicament preferably is administered intravenously, by aerosolization or orally. Preferably, the 2-O desulfated heparin medicament includes a physiologically acceptable carrier which may be selected from the group consisting of physiologically buffered saline, normal saline, and distilled water. Additionally provided is a method of synthesizing 2-O desulfated heparin.

18 Claims, 17 Drawing Sheets

OTHER PUBLICATIONS

Thourani Vinod H. et al., "Nonanticoagulant heparin inhibits NF-κB-activation and attenuates myocardial reperfusion injury", *American Journal of Physiology*, vol. 278, No. 6 Part 2, Jun. 2000, pp. H2084-H2093.

Greinacher Andreas et al., "Characterization of the structural requirements for a carbohydrate based anticoagulant with a reduced risk of inducing the immunological type of heparin-associated thrombocytopenia", *Thrombosis and Haemostasis*, vol. 74, No. 3, 1995, pp. 886-892.

* cited by examiner

# METHOD AND MEDICAMENT FOR SULFATED POLYSACCHARIDE TREATMENT OF HEPARIN-INDUCED THROMBOCYTOPENIA (HIT) SYNDROME

CROSS-REFERENCE TO RELATED APPLICATIONS

This application is a continuation of U.S. application Ser. No. 10/869,370, currently abandoned, filed Jun. 16, 2004 which is hereby incorporated herein in its entirety by reference.

BACKGROUND OF THE INVENTION

1. Field of the Invention

This invention relates to a medicament for treating and preventing platelet activation or thrombosis in the presence of heparin- and platelet factor 4-complex reactive antibodies using a two-O desulfated heparin and to a method for treating.

2. The Prior Art

The drug heparin, discovered almost a century ago, is used even today to prevent coagulation of the blood. Its application ranges from prevention of deep vein thrombosis in medical and surgical patients at risk for venous thrombosis and subsequent pulmonary embolism, to full anticoagulation as treatment of patients suffering pulmonary embolism, myocardial infarction, or other thrombotic disorders, and full anticoagulation in patients undergoing intravascular catheterization procedures or cardiac surgery, so that thrombosis is prevented on catheters or heart-lung bypass machines. Recently, heparin has also been found to be useful to treat disorders of vascular proliferation or inflammation, and has been shown beneficial in a plethora of other diseases, including secondary hypoxic pulmonary hypertension, asthma, cystic fibrosis, inflammatory bowel disease, eczema, burns and glomerulonephritis. However, heparin has two important and serious side effects limiting its use.

The first of these is its major therapeutic indication: excessive bleeding from anticoagulation. While anticoagulation is a benefit in prevention or treatment of thrombotic diseases, this is a drawback if heparin is used to treat other diseases such as asthma where anticoagulation is not needed for therapeutic benefit, and may even pose additional risk to the patient. Untoward bleeding from anticoagulation is even the principal side effect when heparin is used for prevention or treatment of thrombotic disorders where anticoagulation is indicated. Fortunately, the side effect of bleeding is usually self-limited. With termination of heparin therapy and replacement of any blood lost from the vascular space, coagulation function and blood pressure are usually restored to normal in a short time, ending the period of risk.

A second side effect, heparin-induced thrombocytopenia, is less frequent but far more serious. This condition refers to the fall in blood platelet counts occurring in some patients who receive heparin therapy in any form. The condition has been extensively reviewed by several authors (Fabris F, Ahmad S, Cella G, Jeske W P, Walenga J M, Fareed J. Pathophysiology of heparin-induced thrombocytopenia. Clinical and diagnostic implications—a review. *Archiv Pathol Lab Med* 124:1657-1666, 2000; Arepally G, Cines D B. Pathogenesis of heparin-induced thrombocytopenia and thrombosis. *Autoimmunity Rev* 1:125-132, 2002; Warkentin T E, Greinacher A. Heparin-induced thrombocytopenia and cardiac surgery. *Ann Thorac Surg* 76:638-648, 2003; Warkentin T E. Heparin-induced thrombocytopenia: pathogenesis and management. *Brit J Haematol* 121:535-555, 2003; Chong G H. Heparin-induced thrombocytopenia. *J Thromb Haemostas* 1: 1471-1478, 2003).

Two types of heparin-induced thrombocytopenia (HIT) exist. Heparin-induced thrombocytopenia-1 (HIT-1) is characterized by a brief and asymptomatic fall in the platelet count to as low as $100 \times 10^9/L$. This condition resolves spontaneously on its own and does not require discontinuation of the drug. It is thought that this condition is caused by heparin-induced platelet clumping, no immune component of the disease has been identified, and complications of the condition are unusual.

The second type of heparin-induced thrombocytopenia is more deadly. Heparin-induced thrombocytopenia-II (HIT-2) has an immunologic cause and is characterized by a profound fall in the platelet count (>50%) often after the fifth day of heparin therapy. In contrast to HIT-1, in which complications are rare, HIT-2 is usually accompanied by major arterial, venous or microvascular thrombosis, with loss of organ function or limb perfusion. Untreated, the condition can result in death. More common with heparin from bovine lung (5% of patients) than with porcine intestinal heparin (1% of patients), the incidence of the disease has varied widely, depending on the type of heparin, route of administration or patient population.

Intravenous heparin is associated with an overall incidence of HIT-2 of about 1.7%, whereas the condition is rare with subcutaneous prophylactic administration to prevent deep vein thrombosis (Schmitt B P, Adelman B. Heparin-associated thrombocytopenia: a critical review and pooled analysis. *Am J Med Sci* 305:208-215, 1993). Use of low molecular weight but fully anticoagulant heparins such as enoxaparin or dalteparin are less likely to result in the syndrome, but HIT-2 has been reported with low molecular weight heparins. The only anticoagulant thought to be completely free of risk from HIT-2 induction is the recently approved synthetic pentasaccharide factor Xa inhibitor fondaparinux sodium. (Walenga J M, Jeske W P, Bara L, Samama M M, Fareed, J, State-of-the-art article, Biochemical and Pharmacologic rationale for the development of a Heparin pentasaccharide. *Thromb Res* 86(1):1-36 (1997)).

The pathogenesis of HIT-2 is centrally focused upon platelet factor 4 (PF4), a 70-amino acid (7.78 kD) platelet-specific chemokine that is stored in platelet a granules, where it is bound to the glycosaminoglycan chondroitin sulfate. When released, PF4 self-associates into a tetramer of approximately 31 kD. PF4 is highly basic (32 lysine and 12 arginine residues per tetramer), rendering it highly positively charged. Normal plasma levels of PF4 are low, on the order of 8 nmol/L). That PF4 released from platelets following platelet activation binds to the glycocalyx of endothelial cells as a reservoir. The infusion of heparin transiently increases PF4 levels 15 to 30 fold for several hours by displacing PF4 from the vascular endothelial interface.

Formation of the PF4-heparin complex occurs optimally at equivalent stoichiometric concentrations of PF4 and heparin. When administered as a therapeutic anticoagulant, heparin levels range from 0.2 to 0.4 IU/ml, or 100-200 nmol/L, higher than optimum concentrations for PF4-heparin complex formation. However, in patients such as those undergoing cardiac or hip surgery, in vivo activation of platelets occurs, releasing PF4 into the circulation and increasing circulating PF4 levels (to 75-100 nmol/L) toward the optimal concentrations for 1:1 stoichiometric complex formation. When heparin binds to PF4, it produces a conformational change in the protein, exposing antigenic epitopes to which an antibody binds.

The HIT antibody binds heparin-PF4 complexes with high affinity. This antibody-heparin-PF4 complex then binds to platelets by attachment of the antibody Fc domain to the platelet Fc receptor (FcγRIIa). This in turn crosslinks the Fc platelet receptors, inducing platelet activation, thromboxane synthesis and platelet aggregation. PF4 released from the activated, aggregating platelets complexes with additional extracellular heparin to form additional heparin-PF4 complexes which bind to the platelet surface and serve as additional sites for HIT antibody binding. This next wave of HIT antibody binding to platelet-localized heparin-PF4 complexes occurs through the antibody's Fab domain, leaving the Fc domain free to interact with the Fc receptors of adjacent platelets, cross-linking FcγRIIa receptors and inducing additional platelet activation and aggregation. In parallel, platelet activation also results in CD40 ligand/CD40 release and interaction, resulting in the induction of tissue factor expression on the surface of endothelial cells and macrophages. The generation of platelet microparticles when HIT antibodies are present that are highly procoagulant; the up regulation of the adhesion molecule P-selection in the platelet surface; and the induction of a pro-inflammatory state with HIT shows the involvement of neutrophils and monocytes with platelets activated by HIT antibodies as well as cytokine up regulation in the patients. (Walenga J M, Jeske W P, Prechel M M, Makhos M. Newer insights on the mechanism of heparin-induced thrombocytopenia. *Semin Thromb Hemost* 30(Suppl 1):57-67 (2004)). This compounds the hypercoagulable state by providing stimulus for initiation of the extrinsic coagulation cascade, and provides the back-drop for the thrombotic complications of the HIT-2 syndrome. Thrombocytopenia is caused by clearance of activated platelets and platelet aggregates by the reticuloendothelial system.

The clinical syndrome characterizing HIT-2 is distinguished by a substantial fall in the platelet count by usually more than 50% to a median nadir of about $55 \times 10^9$/L. The fall in platelets can be accompanied by development of venous thrombosis and pulmonary embolism, or, less commonly, arterial thrombosis involving the large lower-limb arteries. Thrombotic stroke and myocardial infarction occurs less often. Another feature of the syndrome is the appearance of skin lesions at heparin injection sites, ranging in appearance from erythematous plaques to frank skin necrosis. A quarter of patients develop an acute syndrome of fever, chills, respiratory distress, hypertension and global amnesia when they receive heparin intravenously at a time when circulating HIT-2 antibodies are present. Even disseminated intravascular coagulation may result. To prevent these complications, it is suggested that when HIT-2 is recognized, the precipitating heparinoid should be stopped and the patient fully anticoagulated with an alternative agent such as a direct thrombin inhibitor (lepirudin, argatroban or bivalirudin) or the synthetic pentasaccharide fondaparinux, which does not cross-react with HIT antibodies. Because the use of warfarin acutely in the setting of HIT-2 has been associated with development of microvascular thrombosis or skin necrosis, long term follow-up anticoagulation with warfarin is delayed until resolution of thrombocytopenia. This often necessitates prolonged hospitalization for administration of alternative anticoagulants such as the direct thrombin inhibitors.

The structural features of heparinoids that are associated with HIT-2 have been characterized in detail (Greinacher A, Alban S, Dummel V, Franz G, Mueller-Eckhardt C, Characterization of the structural requirements for a carbohydrate based anticoagulant with a reduced risk of inducing the immunological type of heparin-associated thrombocytopenia. *Thromb Haemostas* 74:886-892 (1995); Walenga J M, et al, supra (2004); Walenga J M, Koza M J, Lewis B E, Pifarré R. Relative heparin induced thrombocytopenic potential of low molecular weight heparins and new antithrombotic agents. *Clin Appl Thromb Hemost.* 2(Suppl 1):S21-S27 (1996); and Jeske W P, Jay A M, Haas S, Walenga J M. Heparin-induced thrombocytopenic potential of GAG and non-GAG-based antithrombotic agents. *Clin Appl Thromb Hemost* 5(Suppl 1):S56-S62 (1999)). With linear heparin-like carbohydrate sulfates, the risk of platelet activation in the presence of a HIT antibody and PF4 was critically dependent upon both the molecular weight of the polymer and its degree of sulfation (i.e., average number of sulfates per carbohydrate monomer). The critical degree of sulfation to form the HIT-reactive heparin-PF4 antigenic complex was found to lie between 0.6 and 1.20 (i.e., 0.6 to 1.2 sulfate groups per carbohydrate monomer). The tendency of a sulfated polysaccharide to form the HIT reactive heparin-PF4 antigenic complex, with subsequent platelet activation, was also governed by molecular weight. Increasing concentrations of heparin were required for complex formation as heparins with decreasing molecular weight down to 2.4 kD were studied. With saccharides below 2.4 kD, no complex formation was observed. HIT antibody activation was also not observed with the synthetic pentasaccharide fondaparinux, which weighs about 1.7 kD. The investigators concluded that only two strategies predictably reduced the risk of HIT-reactive heparin-PF4 complex formation: 1) reducing degree of sulfation to <0.6 sulfates per carbohydrate unit; or 2) decreasing the molecular weight of the polysaccharide to <2.4 kD.

A heparin-like compound that does not interact with PF4 to form HIT-antibody reactive complexes would offer major advantages over unfractionated or low molecular weight heparins currently available for therapeutic use. Although there is no clinical proof as an anticoagulant, the new pentasaccharide fondaparinux appears to have achieved that goal, since it does not activate platelets in the presence of HIT antibody (Greinacher A, et al., supra; Walenga J M, et al, supra (2004); Walenga J M, et al., supra (1996); and Jeske W P, et al., supra (1999)). However, while ideal as an anticoagulant agent, this small molecular weight heparin analog is fully anticoagulant, placing the treated patient at risk for excess bleeding if he has a bleeding diathesis or rent in the integrity of his vascular system. This is especially problematic in subjects with HIT who have also suffered gastrointestinal or central nervous system hemorrhage. Anticoagulation with fondaparinux or any agent is necessary in HIT to prevent potentially fatal arterial or venous thrombosis, but can be life threatening if the subject is also actively hemorrhaging. Moreover, even if the subject is not hemorrhaging, a low anticoagulant strategy for treating HIT would be far safer and more preferable than the currently available strategies which are all fully anticoagulant drugs and which include the direct thrombin inhibitors, argatroban and lepirudin.

The present invention accomplishes this objective. A 2-O desulfated heparin has been synthesized which is useful as an agent to inhibit inflammation such as ischemia-reperfusion injury of the heart from myocardial infarction. It is an advantage of the present invention that methods to produce this 2-O desulfated heparin (ODS heparin) in large quantities on a commercial scale have been provided. ODS heparin also has greatly reduced USP and anti-Xa anticoagulant activity, rendering it safer for use in anti-inflammatory doses and less likely to cause bleeding. The average molecular weight of 2-O desulfated heparin is 10.5 kD, and its approximate degree of sulfation is 1.0 (5 sulfate groups per pentasaccharide, see FIG. 1), placing it well within the risk range for HIT antibody interaction (Greinacher A, et al., supra). Surprisingly and in spite of size and degree of sulfation which would predict otherwise, ODS heparin does not cause platelet activation in the presence of known HIT-reactive antiserum at low or high concentrations. Thus, ODS heparin also constitutes a safer alternative to other anti-inflammatory heparins by presenting significantly reduced risk for HIT-2 associated thrombocytopenia and thrombosis.

Even more surprisingly, 2-O desulfated heparin is also useful to treat the HIT syndrome once established and reduce the activity of platelet aggregation from an antibody directed against the heparin-PF4 complex. Thus, the administration of 2-O desulfated heparin, which has greatly reduced anticoagulant activity and bleeding risk, could be used as a clinical treatment for HIT syndrome, eliminating the need for risky, fully anticoagulant treatments currently in use for HIT therapy.

SUMMARY OF THE INVENTION

It is an object of the present invention to provide a method for producing a heparin analog that does not produce platelet activation in the presence of serum containing HIT antibodies.

It is a further object of this invention to provide a heparin analog that can be used to treat the established HIT syndrome and prevent platelet aggregation and vascular thrombosis resulting from this condition.

It is another object of this invention to provide a heparin analog that is sufficiently large enough in size and possessing of sufficient degree of retained sulfation as to be anti-inflammatory.

A further object of this invention to provide a heparin analog that substantially does not induce anti-coagulant activity.

As another object of the present invention there is provided a method for using a therapeutic agent which can be used to treat established HIT syndrome without inducing anticoagulant activity.

It is an even further object of this invention that the therapeutic agent is produced from a toxicologically characterized compound.

Also, another object of the present invention is that the synthesis of 2-O desulfated heparin can be produced at commercially feasibly levels.

The present invention provides a heparin medicament free of HIT reactivity or risk comprising a treatment effective amount of 2-O desulfated heparin in a physiologically acceptable carrier. The physiologically acceptable carrier may be selected from the group consisting essentially of physiologically buffered saline, normal saline and distilled water. The medicament preferably comprises a dose of between 2 mg/kg patient body weight and 100 mg/kg, but preferably 3.5-25 mg/kg. These doses are also provided in a physiologically acceptable carrier.

The invention also provides a heparin medicament substantially free of HIT reactivity or risk that has a molecular weight greater than 2.4 kD and a degree of sulfation of greater than 0.6. The invention also provides a heparin medicament that can actively suppress interaction of a HIT antibody with its antigenic determinants and decrease the resulting platelet aggregation and procoagulant state induced by the HIT syndrome.

In preferred embodiments of the invention the 2-O desulfated heparin analog free of HIT reactivity or risk can be administered by aerosolization, by intravenous injection, by subcutaneous injection, orally or by rectal instillation. An effective dose for administration to a human, especially when used intravenously, is a dose between 2 mg/kg and 100 mg/kg of 2-O desulfated heparin. In other embodiments of the invention, the molecular weight is greater than 2.4 kD. In another embodiment of the invention, the degree of sulfation is greater than 0.6 but less than 1.2. Preferably, the medicament includes a physiologically acceptable carrier which may be selected from the group consisting of physiologically buffered saline, normal saline, and distilled water.

The present invention further provides a method of producing a heparin analog substantially free of HIT antibody reactivity or risk and can be also used effectively to actively treat the HIT syndrome, which method comprises reducing heparin in solution and lyophilizing the reducing heparin solution. In another embodiment, the heparin analog substantially free of HIT antibody reactivity or risk and also useful in the treatment of the HIT syndrome is produced by lyophilizing heparin in solution without reducing it. In a preferred embodiment, the pH of the reduced or non-reduced heparin solution is raised above 13.

BRIEF DESCRIPTION OF THE DRAWINGS

The foregoing and other objects, advantages and features of the invention, and manners in which the same are accomplished, would become apparent from the following detailed description of the invention taken in conjunction with the accompanying drawings which illustrate preferred and exemplary embodiments, wherein.

DETAILED DESCRIPTION OF THE INVENTION

Figure 1:
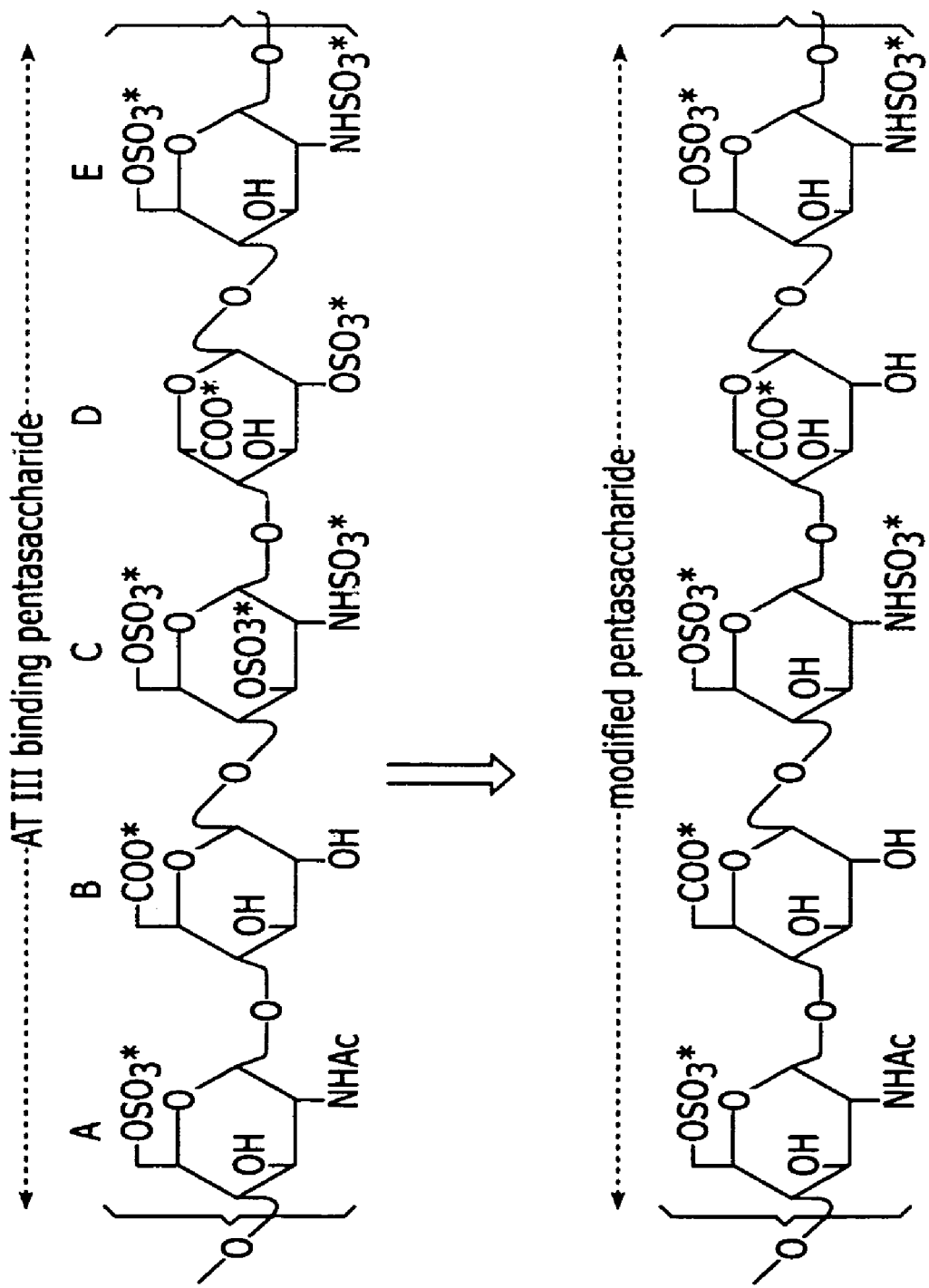
FIG. 1 shows a chemical formula of the pentasaccharide binding sequence of unfractionated heparin and the comparable sequence of 2-O, 3-O desulfated heparin (ODS heparin)

The present invention will now describe more fully hereinafter with reference to the accompanying examples, in which preferred embodiments of the invention are shown. Indeed, these inventions, may be embodied in many different forms and should not be construed as limited to the embodiments set forth herein; rather these embodiments are provided so that this disclosure will be thorough and complete, and will fully convey the scope of the invention to those skilled in the art.

It has been found that heparin in larger than usual anticoagulant doses and a variety of nonanticoagulant heparins (N-desulfated; 2-O, 3-O or 6-O desulfated; N-desulfated and reacetylated; and O-decarboxylated heparin) can attenuate inflammatory responses in vivo, such as inhibiting the destructive effects of human leukocyte elastase (HLE) on lung when instilled in the trachea. These same heparins and nonanticoagulant heparins can attenuate ischemia-reperfusion injury in the heart, brain and other organs and reduce the size of organ infarction as measured by the size of organ necrosis. Examples of the preparation of 2-O desulfated nonanticoagulant heparin, which is also 3-O desulfated, may be found in, for example, U.S. Pat. Nos. 5,668,188; 5,912, 237; and 6,489,311, incorporated herein by reference. The amounts of 2-O desulfated heparin may be given in amounts of 2 mg/kg to 100 mg/kg, but preferably in amounts from about 3.5 mg/kg to 25 mg/kg. The nonanticoagulant heparin 2-O desulfated heparin has the advantage of inhibiting inflammation such as HLE-induced lung inflammation or myocardial inflammation induced by ischemia-reperfusion, but without the side effect of excessive anticoagulation that would result from equivalent doses of unmodified heparin. Other nonanticoagulant heparins, low molecular weight heparins (Yanaka K, Spellman S R, McCarthy J B, Oegema T R Jr, Low W C, Camarata P J., Reduction of brain injury using heparin to inhibit leukocyte accumulation in a rat model of transient focal cerebral ischemia. I. Protective mechanism. *J Neurosurg* 85:1102-1107, 1996) and sulfated polysaccharide heparin analogs (Kilgore K S, Naylor K B, Tanhehco E J, Park J L, Booth E A, Washington R A, Lucchesi B R., The semi-synthetic polysaccharide pentosan polysulfate prevents complement-mediated myocardial injury in the rabbit perfused heart. *J Pharmacol Exp Therap* 285:987-994, 1998) can also inhibit inflammation. However these and other heparins and sulfated glycosaminoglycan heparin analogs react with heparin antibodies to form glycosaminoglycan-PF4-HIT-reactive antibody complexes capable of inducing platelet activation and the HIT-2 thrombotic syndrome. This potentially deadly risk severely limits the use of nonanticoagulant heparins as anti-inflammatory therapies.

The only sulfated polysaccharide that might be predictably employed without risk of the HIT-2 thrombotic syndrome is the synthetic anticoagulant pentasaccharide fondaparinux (Greinacher A, et al., supra). This ultra-low molecular weight heparin analog is an effective anticoagulant but is less useful for treating inflammation because it is fully anticoagulant and therefore at risk of inducing bleeding, and because its small size greatly reduces its activity in blocking selectin mediated PMN attachment (Koenig A, et al., supra).

The structural requirements for a sulfated carbohydrate free from HIT-antibody reactivity have been characterized as <2.4 kD in molecular weight and a degree of sulfation of <0.6 sulfates per carbohydrate moiety (Greinacher A, et al., supra). With linear sulfated polysaccharides of a constant chain length of 35 monosaccharides, the critical degree of sulfation to form the HIT antigen was between 0.6 and 1.2 sulfates per monosaccharide. For sulfated carbohydrates in the range of commercially available heparins, HIT-mediated platelet activation was maximal at a degree of sulfation of 1.25. Platelet activation in the presence of linear sulfated polysaccharides with a fixed degree of sulfation was also dependent upon molecular weight, with decreasing concentrations of sulfated polysaccharide needed for 50% maximal HIT-mediated platelet activation as molecular weight was increased. As an example, a concentration of 50 nmol/L of sulfated polysaccharide was required for 50% maximal platelet activation at a molecular weight of 12.2 kD, approximately that of commercial unfractionated heparin. This concentration is close to the optimal heparin concentration for elicitation of the HIT-2 syndrome clinically. In the case of heparin, the optimum molecular weight was actually found to be 4.8 kD (a hexadecasaccharide), near the molecular weight of commercially available low molecular weight heparins, but higher molecular weights also supported HIT-mediated platelet activation. Branched chain sulfated carbohydrates were able to form the HIT antigen with PF4 at even lower degrees of sulfation and molecular weight. Walenga J M, et al, supra (2004); Walenga J M, et al., supra (1996); and Jeske W P, et al., supra). Only sulfated polysaccharides with a molecular weight of less than 2.4 kD or a degree of sulfation of less than 0.6 sulfate groups per monosaccharide were free of HIT reactivity. As an example, the fully anticoagulant pentasaccharide fondaparinux, with a molecular weight of 1.78 kD, failed to produce any platelet activation in the presence of HIT antibodies, regardless of the concentration of pentasaccharide used.

The partially desulfated heparin 2-O desulfated heparin is produced as outlined in U.S. Pat. Nos. 5,668,188; 5,912,237; and 6,489,311, by reducing heparin in solution and drying, lyophilizing or vacuum distilling the reduced heparin solution. One can place the starting heparin in, for example, water or other solvent. The typical concentration of the heparin solution can be from 1 to 10 percent heparin. The heparin used in the reaction can be obtained from numerous sources, known in the art, such as porcine intestine or beef lung. One can utilize heparin that has been modified in any number of ways known to those of skill in the art, such as lower molecular weight heparins produced by periodate oxidation or nitrous acid depolymerization. One can also use as starting material the currently available fully anticoagulant low molecular weight heparins enoxaparin or dalteparin. Other possible starting materials will be apparent to those of skill in the art, given the teaching provided herein.

The selected heparin starting material in solution can be reduced in solution by incubating it with a reducing agent, such as sodium borohydride, catalytic hydrogen, or lithium aluminum hydride. A preferred reduction of heparin is performed by incubating the heparin with sodium borohydride, typically at a concentration (wt/vol) of 1%, or 10 grams of NaBH4 per liter of solution. Additionally, other known reducing agents can be utilized. The incubation with reducing substance can be achieved over a wide range of temperatures, taking care that the temperature is not so high that the heparin caramelizes. A suggested temperature range is about 4 to 30° C., or preferably about 20-25° C. The length of the incubation can also vary over a wide range as long as it is sufficient for reduction to occur. For example, several hours to overnight (i.e., about 4 to about 12 hours) can be sufficient. However, the time can be extended to over several days, for example, exceeding about 60 hours. Alternatively to reduction of the heparin, which preserves its molecular weight during lyophilization, one can omit this step and proceed directly to lyophilization or drying for production. However, depolymerization will occur more intensely without the reducing step and the molecular weight of the resulting product will be predictably lower.

Additionally, the method for producing 2-O desulfated heparin further comprises raising the pH of the reduced or unreduced heparin to 13 or greater by adding a base capable of raising the pH to 13 or greater to the reduced or non-reduced heparin solution. The pH can be raised by adding any of a number of agents including hydroxides, such as sodium, potassium or barium hydroxide. A preferred agent is sodium hydroxide (NaOH). Once a pH of 13 or greater has been achieved, it can be beneficial to further increase the concentration of the base. For example, it is preferable to add NaOH to a concentration of about 0.25 M to about 0.5 M NaOH. This alkaline solution is then dried, lyophilized or vacuum distilled.

The partially desulfated heparin produced by such methods as outlined in U.S. Pat. Nos. 5,668,188; 5,912,237; and 6,489,311, is a 2-O desulfated heparin that is also largely 3-O desulfated and possesses a degree of sulfation of approximately 1.0 (5 sulfate groups per pentasaccharides; see FIG. 1). If unfractionated porcine heparin with an average molecular weight of 11.5 kD is used as a starting material and this is reduced with sodium borohydride prior to lyophilization, the resulting product has an average molecular weight of 10.5 kD. With a degree of sulfation of 1.0 and a molecular weight of 10.5 kD, this heparin analog would be predicted to significantly trigger platelet activation in the presence of a HIT antibody and PF4. Whereas unfractionated heparin actively stimulates platelet activation under these circumstances when provided in concentrations of 0.4 µmoles/L, the usual therapeutic anticoagulating concentration of this drug, the 2-O desulfated heparin analog by the method described does not activate platelets when studied in concentrations ranging from 0.78 µmoles/L to 100 µmoles/L. These results are obtained when platelet activation is studied by release of $^{14}C$-serotinin from platelets or when platelet activation is measured by formation of microparticles, detected using flow cytometry. The examples to follow will illustrate these points in detail. That 2-O desulfated heparin does not induce the HIT antigen in the presence of HIT antibody is a major advantage, making it therapeutically safer as a heparin analog for use in treating inflammatory and other conditions where a heparinoid might be indicated or useful.

Even more surprisingly, 2-O desulfated heparin not only fails to trigger HIT-like platelet activation, but is also itself effective for suppressing activation of platelets when they are exposed to unmodified heparin in the presence of serum from patients with the clinical HIT syndrome. For HIT platelet activation, amelioration of serotonin release was observed at a concentration of 2-O desulfated heparin as low as 3.13 μg/ml when in the test system where low antithrombotic concentrations of heparin were added to platelets and HIT sera. A higher concentration (6.25 μg/ml) was needed to initiate amelioration when higher anticoagulant concentrations of heparin were added to platelets and HIT sera. Complete amelioration of serotonin release was observed at 25 μg/ml and higher concentrations of 2-O desulfated heparin. When the test system of HIT platelet activation was microparticle formation from activated platelets, amelioration was seen at concentrations of 2-O desulfated heparin as low as 6.25 μg/ml in test systems with both 0.1 and 0.5 U/ml of heparin used to activate platelets in the presence of HIT sera. Complete amelioration of platelet microparticle formation in response to heparin and HIT sera was achieved at 2-O desulfated heparin concentrations of 50 μg/ml. Finally, when platelet activation was measured as P-selectin (CD62) expression on the platelet surface, concentrations of 2-O desulfated heparin as low as 1.56 μg/ml ameliorated platelet activation in the presence of HIT sera and 0.1 or 0.5 U/ml unfractionated heparin. Complete amelioration of platelet P-selectin expression was seen with 2-O desulfated heparin concentrations >25 μg/ml. Overall, considering the three methods of measuring platelet activation, 2-O desulfated heparin was effective in suppressing HIT-induced platelet activation beginning at 6.25 μg/ml and HIT-induced platelet activation was completely suppressed at 50 μg/ml of 2-O desulfated heparin. These are concentrations of 2-O desulfated heparin that can be achieved in vivo with modest doses of the drug.

Depending upon the intended mode of administration, the pharmaceutical compositions may be in the form of a solid, semi-solid or liquid dosage forms, such as, for example, tablets, suppositories, pills, capsules, powders, liquids, suspensions, lotions, creams, gels, or the like, preferably in unit dosage form suitable for single administration of a precise dosage. The compositions will include an effective amount of the selected drug in combination with a pharmaceutically acceptable carrier and, in addition, may include other medicinal agents, pharmaceutical agents, carriers, adjuvants, diluents, and the like.

The invention additionally provides aerosol particles comprising a physiologically acceptable carrier and an effective amount of 2-O desulfated heparin or analog thereof. The particles can consist of essentially of particles less than 10 microns and preferably less than 5 microns. For delivery to the airway or lung, 2-O desulfated heparin can be delivered as a micronized powder or inhaled as a solution with the use of a commercially available nebulizer device. For delivery to the nasal mucosa, 2-O desulfated heparin can be administered as a solution that is aerosolized by a commercially available misting or spray device, or it can be delivered as a nasally administered micronized dry powder.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc. an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, and triethanolamine oleate. Liquid compositions can be aerosolized for administration. Actual methods of preparing such dosage forms are known, or will be apparent, to those skilled in this art; for example, see *Remington's Pharmaceutical Sciences,* E.W. Martin (ed.), Mack Publishing Co., Easton, Pa.

For oral administration, fine powders or granules may contain diluting, dispersing, and/or surface active agents, and may be presented in water or in a syrup, in capsules or sachets in the dry state, or in a non-aqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated. To enhance oral penetration and gastrointestinal absorption, 2-O-desulfated heparin can be formulated with mixtures of olive oil, bile salts, or sodium N-[8-(2 hydroxybenzoyl)amino] caprylate (SNAC). A preferable ratio of about 2.25 g of SNAC to 200 to 1,000 mg 2-O desulfated heparin is employed. Additional formulations that facilitate gastrointestinal absorption can be made by formulating phospholipids-cation precipitate cochleate delivery vesicles of 2-O desulfated heparin with phosphotidylserine and calcium, using methods described in U.S. Pat. Nos. 6,153,217; 5,994,318; 5,840,707, among others.

For rectal administration, 2-O desulfated heparin can be administered in a suppository, foam, gel, solution or enema.

Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, which is incorporated by reference herein.

By "pharmaceutically acceptable" is meant a material that is not biologically or otherwise undesirable, i.e., the material may be administered to an individual along with the 2-O, 3-O desulfated heparin or heparin analog without causing any undesirable biological effects or interacting in a deleterious manner with any of the other components of the pharmaceutical composition in which it is contained.

The present invention is more particularly described in the following examples which are intended as illustrative only since numerous modifications and variations therein will be apparent to those skilled in the art.

EXAMPLES

Example I

Production of 2-O Desulfated Heparin that is Nonanticoagulant, does not Activate Platelets in the Presence of a Heparin-Induced Thrombocytopenia Antibody, and Even Ameliorates Platelet Activation Induced by Heparin in the Presence of a Heparin-Induced Thrombocytopenia Antibody Partially desulfated 2-O desulfated heparin can be produced in commercially practical quantities by methods described in U.S. Pat. Nos. 5,668,188; 5,912,237; and 6,489,311. Heparin modification (to ODS heparin) was made by adding 500 gm of porcine intestinal mucosal sodium heparin from lot EM3037991 to 10 L deionized water (5% final heparin concentration). Sodium borohydride was added to 1% final concentration and the mixture was incubated overnight at 25° C. Sodium hydroxide was then added to 0.4 M final concentration (pH greater than 13) and the mixture was lyophilized to dryness. Excess sodium borohydride and sodium hydroxide were removed by ultrafiltration. The final product was adjusted to pH 7.0, precipitated by addition of three volumes of cold ethanol and dried. The 2-O desulfated heparin produced by this procedure was a fine crystalline slightly off-white powder with less than 10 USP units/mg anticoagulant activity and less than 10 anti Xa units/mg anticoagulant activity. The structure of this heparin is shown in FIG. 1. Molecular weight was determined by high performance size exclusion chromatography in conjunction with multiangle laser light scattering, using a miniDAWN detector (Wyatt Technology Corporation, Santa Barbara, Calif.) operating at 690 nm. Compared with an average molecular weight of 13.1 kD for the starting material, ODS Heparin had an average molecular weight of 11.8 kD.

Figure 2:
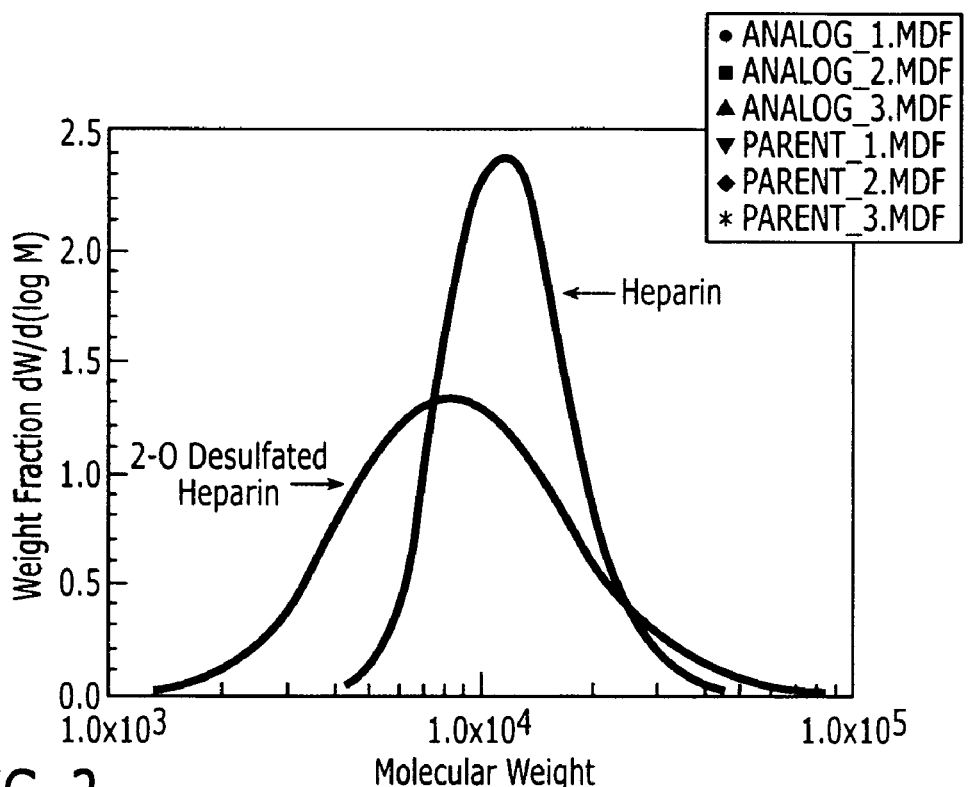
FIG. 2 shows the differential molecular weight distribution plots determined by multi-angle laser light scattering, in conjunction with high performance size exclusion chromatography, of the ODS heparin compared to the parent porcine intestinal heparin from which it was produced.
Figure 3A:
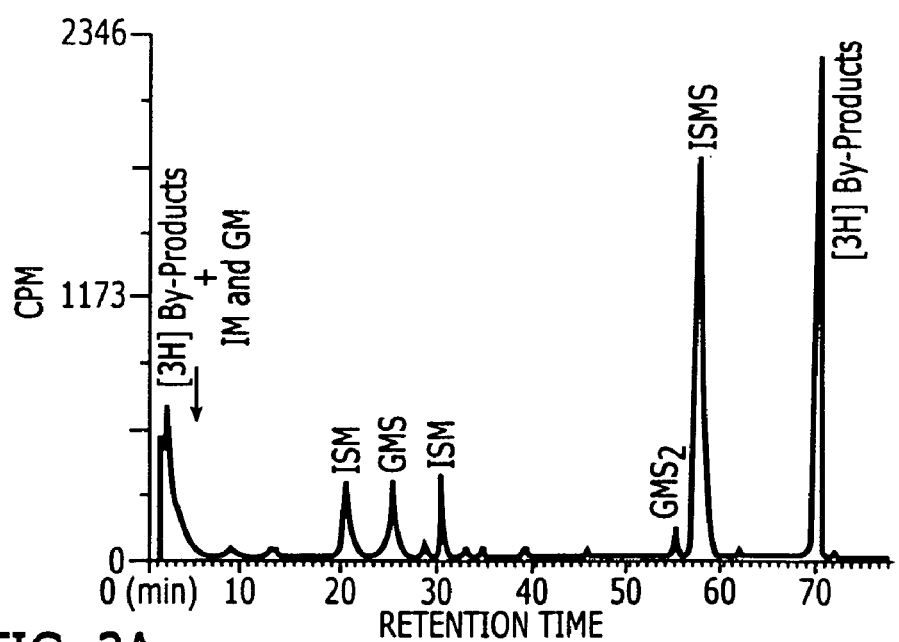
FIG. 3 shows disaccharide analysis of heparin and the ODS heparin of this invention.
Figure 3B:
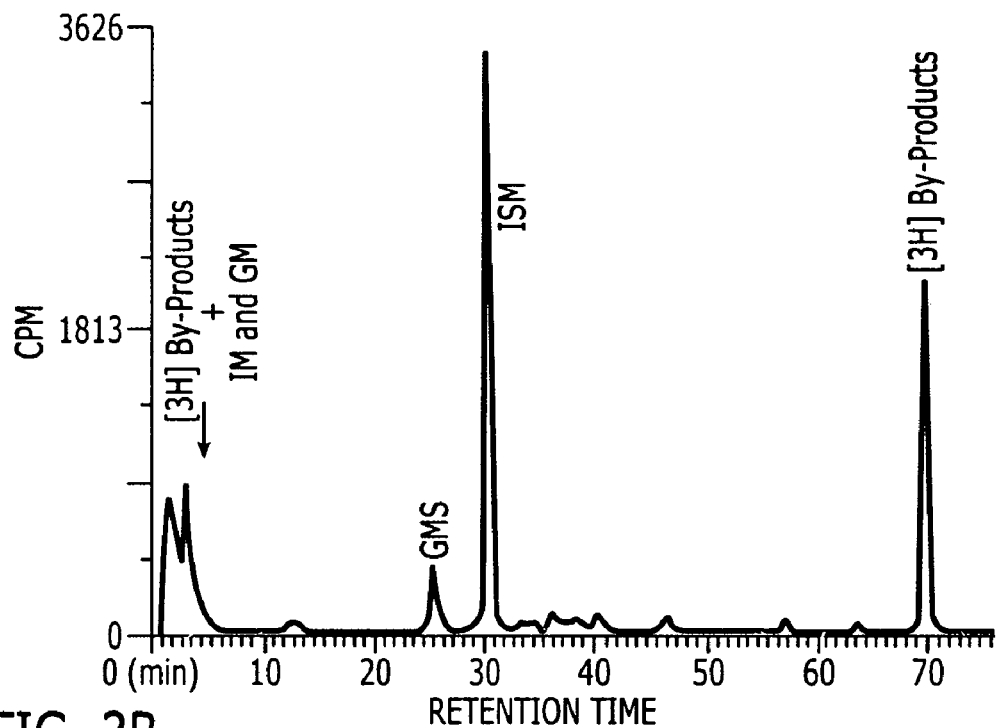
Figure 4:
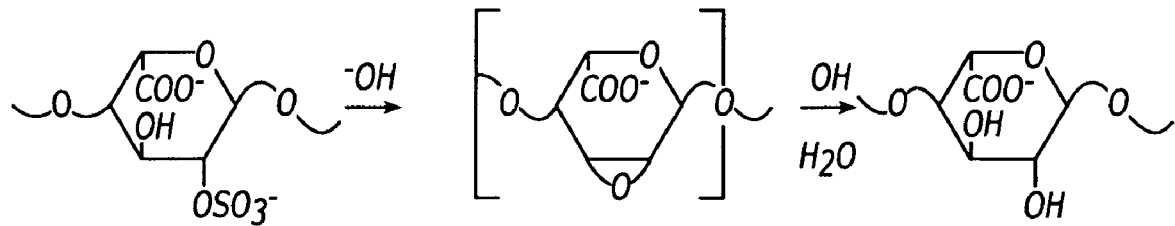
FIG. 4 shows a proposed reaction scheme for desulfating the 2-O position of $\alpha$-L-iduronic acid in the pentasaccharide binding sequence of heparin.

Demonstrated in FIG. 2 are the differential molecular weight distributions of the parent molecule and ODS heparin. Disaccharide analysis was performed by the method of Guo and Conrad (Guo Y, Conrad H E, Analysis of oligosaccharides from heparin by reversed-phase ion-pairing high performance liquid chromatography. *Anal Biochem* 178:54-62, 1988). Compared to the starting material shown in FIG. 3A, ODS heparin is a 2-O desulfated heparin (shown in FIG. 3B) characterized by conversion of ISM [L-iduronic acid(2-sulfate)-2,5-anhydromannitol] to IM [L-iduronic acid-2,5-anhydromannitol], and ISMS [L-iduronic acid(2-sulfate)-2,5 anhydromannitol(6-sulfate)] to IMS L-iduronic acid-2,5-anhydromannitol(6-sulfate), both indicating 2-O desulfation. The proposed sequence of 2-O desulfation is shown in FIG. 4. ODS heparin is also a 3-O desulfated heparin, characterized by conversion of GMS2 [D47 glucuronic acid-2,5-anhydromannitol(3,6-disulfate)] to GMS [D-glucuronic acid-2,5-anhydromannitol(6-sulfate)],indicating 3-O desulfation.

The potential of this 2-O, 3-O desulfated heparin to interact with HIT antibody and active platelets was studied using donor platelets and serum from three different patients clinically diagnosed with HIT-2 by manifesting thrombocytopenia related to heparin exposure, correction of thrombocytopenia with removal of heparin, and a positive platelet activation test, with or without thrombosis. Two techniques were employed to measure platelet activation in response to heparin or 2-O desulfated heparin in the presence of HIT-reactive serum.

The first technique was the serotonin release assay (SRA), considered the gold standard laboratory test for HIT, and performed as described by Sheridan (Sheridan D, Carter C, Kelton J C, A diagnostic test for heparin-induced thrombocytopenia. *Blood* 67:27-30, 1986). Washed platelets were loaded with $^{14}$C serotonin ($^{14}$C-hydroxy-tryptamine-creatine sulfate, Amersham), and then incubated with various concentrations of test heparin or heparin analog in the presence of serum from known HIT-positive patients as a source of antibody. Activation was assessed as $^{14}$C serotonin release from platelets during activation, with $^{14}$C serotonin quantitated using a liquid scintillation counter. Formation of the heparin-PF4-HIT antibody complex results in platelet activation and isotope release into the buffer medium. Activated platelets are defined as % isotope release of ≧20%.

Specifically, using a two-syringe technique whole blood was drawn from a volunteer donor into sodium citrate (0.109 M) in a ratio of 1 part anticoagulant to 9 parts whole blood. The initial 3 ml of whole blood in the first syringe was discarded. The anticoagulated blood was centrifuged (80×g, 15 min, room temperature) to obtain platelet rich plasma (PRP). The PRP was labeled with 0.1 μCi $^{14}$C-serotonin/ml (45 min, 37° C.), then washed and resuspended in albumin-free Tyrode's solution to a count of 300,000 platelets/μl. HIT serum (20 μl) was incubated (1 hour @ room temperature) with 70 μl of the platelet suspension, and 5 μl of 2-O desulfated heparin (0, 0.78, 1.56, 3.13, 6.25, 12.5, 25, 50 and 100 μg/ml final concentrations). For system controls, 10 μl unfractionated heparin (UFH; either 0.1 or 0.5 U/ml final concentrations, corresponding to the concentrations in plasma found in patients on anti-thrombotic or fully anticoagulant doses, respectively) was substituted for the 2-O desulfated heparin in the assay. EDTA was added to stop the reaction, and the mixture was centrifuged to pellet the platelets. $^{14}$C-serotonin released into the supernatant was measured on a scintillation counter. Maximal release was measured following platelet lysis with 10% Triton X-100. The test was positive if the release was ≧20% serotonin with 0.1 and 0.5 U/ml UFH (no added 2-O desulfated heparin) and <20% serotonin with 100 U/ml UFH. The test was for cross-reactivity of the HIT antibodies with the 2-O desulfated heparin if ≧20% serotonin release occurred.

The second technique was flow cytometric platelet analysis. In this functional test, platelets in whole blood are activated by heparin or heparin analog in the presence of heparin antibody in serum from a patient clinically diagnosed with HIT. Using flow cytometry, platelet activation was determined in two manners: by the formation of platelet microparticles and by the increase of platelet surface bound P-selectin. Normally, platelets in their unactivated state do not express CD62 on their surface, and platelet microparticles are barely detectable. A positive response is defined as any response significantly greater than the response of the saline control.

Specifically, whole blood drawn by careful double-syringe technique was anticoagulated with hirudin (10 μg/ml final concentration). An aliquot of whole blood (50 μl) was immediately fixed in 1 ml 1% paraformaldehyde (gating control). HIT serum (160 μl) and 2-O desulfated heparin (50 μl; 0, 0.78, 1.56, 3.13, 6.25, 12.5, 25, 50 and 100 μg/ml final concentrations) were added to the whole blood (290 μl) and incubated (37° C., 15 minutes with stirring at 600 rpm). Aliquots (50 μl) were removed and fixed in 1 ml paraformaldehyde (30 minutes, 4° C.). The samples were centrifuged (350 g, 10 minutes) and the supernatant paraformaldehyde removed. The cells were resuspended in calcium-free Tyrode's solution (500 μl, pH 7.4±0.1). 150 μl cell suspension was added to 6.5 μl fluorescein isothiocyanate (FITC) labeled anti-CD61 antibody (Becton-Dickinson; San Jose, Calif.; specific for GPMa on all platelets). Samples are incubated (30 minutes, room temperature) in the dark. All antibodies were titrated against cells expressing their specific antigen prior to experimentation to assess the saturating concentration. Samples were analyzed on an EPICS XL flow cytometer (Beckman-Couter; Hialeah, Fla.) for forward angle (FALS) and side angle light scatter, and for FITC and PE fluorescence. Prior to running samples each day, a size calibration was made by running fluorescent-labeled beads of known size (Flow-Check; Coulter) and adjusting the gain so that 1.0 μm beads fall at the beginning of the second decade of a 4-decade log FALS light scatter scale. A threshold discriminator set on the FITC signal was used to exclude events not labeled with anti-CD61 antibody (non-platelets).

Using the gating control sample, amorphous regions were drawn to include single platelets and platelet microparticles. Platelet microparticles were distinguished from platelets on the basis of their characteristic flow cytometric profile of cell size (FALS) and FITC fluorescence (CD61 platelet marker).

Platelet micro-particles were defined as CD61-positive events that were smaller than the single, nonaggregated platelet population (<~1 µm). 20,000 total CD61-positive events (platelets) were collected for each sample. Data was reported as a percentage of the total number of CD61-positive events analyzed. In testing for cross-reactivity with a heparin-dependent HIT antibody, the UFH controls (no 2-O desulfated heparin) should show a positive response (increased percentage of CD61 positive events in the platelet microparticle region at 0.1 and 0.5 U/ml UFH but not at 100 U/ml UFH). The test was positive for cross-reactivity of the HIT antibodies with the 2-O desulfated heparin if an increase in platelet microparticle formation occurred.

The quantitation of P-selectin expression induced on the surface of platelets by HIT-related platelet activation was determined as follows. To quantitate platelet surface expression of P-selection, platelet-rich plasma was collected and platelets were labeled as described above, but additionally labeled with 6.5 µl of phycoerythrin (PE) labeled antibody (Becton-Dickinson; specific for P-selectin expressed on activated platelets). The gating control sample was used to establish the regions of single platelets and platelet microparticles based on FALS and CD61-FITC fluorescence. A histogram of PE fluoresce (P-selectin expression) was gated to exclude platelet aggregates. A marker encompassing the entire peak was set in order to determine the median P-selectin fluorescence. Results were reported in mean fluorescence intensity units (MFI) of CD62 in the non-aggregated platelet population. In testing for cross-reactivity with a heparin-dependent HIT antibody, the UFH controls should show a positive response (increased median P-selectin fluorescence) at 0.1 and 0.5 U/ml UFH but not at 100 U/ml UFH. The test was positive for cross-reactivity of the HIT antibodies with the 2-O desulfated heparin if an increase in platelet P-selectin expression occurred.

Figure 5:
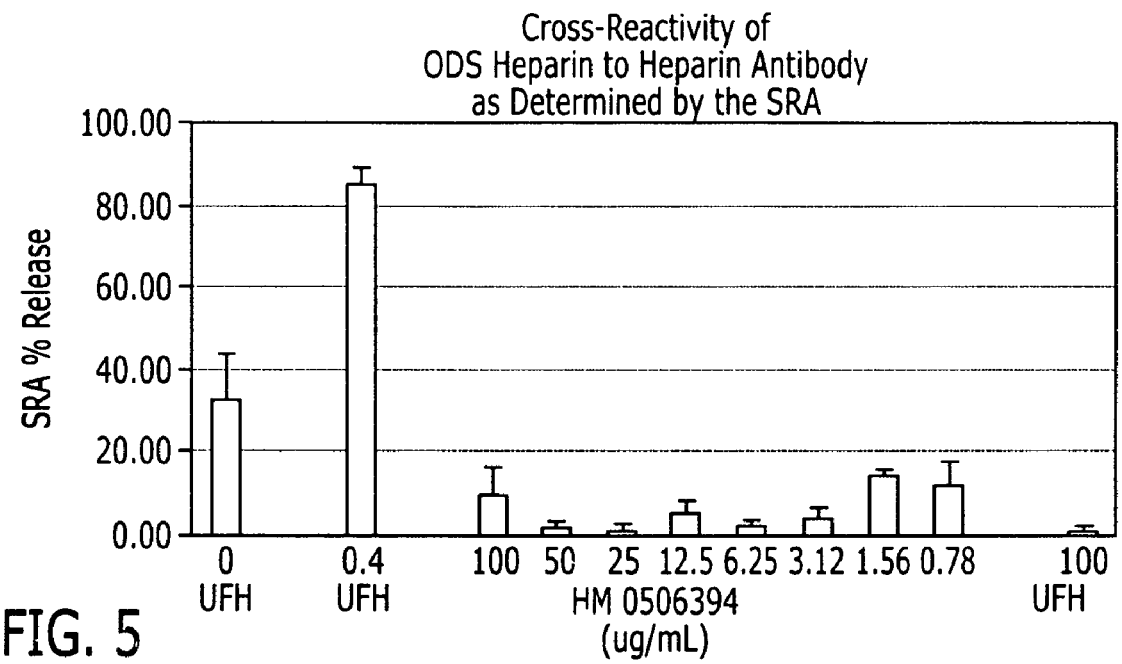
FIG. 5 shows cross-reactivity of the 2-O desulfated heparin of this invention to heparin antibody as determined by the serotonin release assay.

FIG. 5 shows that unfractionated heparin at the usual therapeutic anticoagulant concentration of 0.4 µg/ml elicits release of >80% of total radio labeled serotonin in this system. In contrast, the 2-O desulfated heparin, studied in a range of concentrations from 0.78 to 100 µg/ml, fails to elicit substantial $^{14}C$ serotonin release, indicating that this 2-O desulfated heparin does not interact with a pre-formed HIT antibody causing platelet activation.

Figure 6:
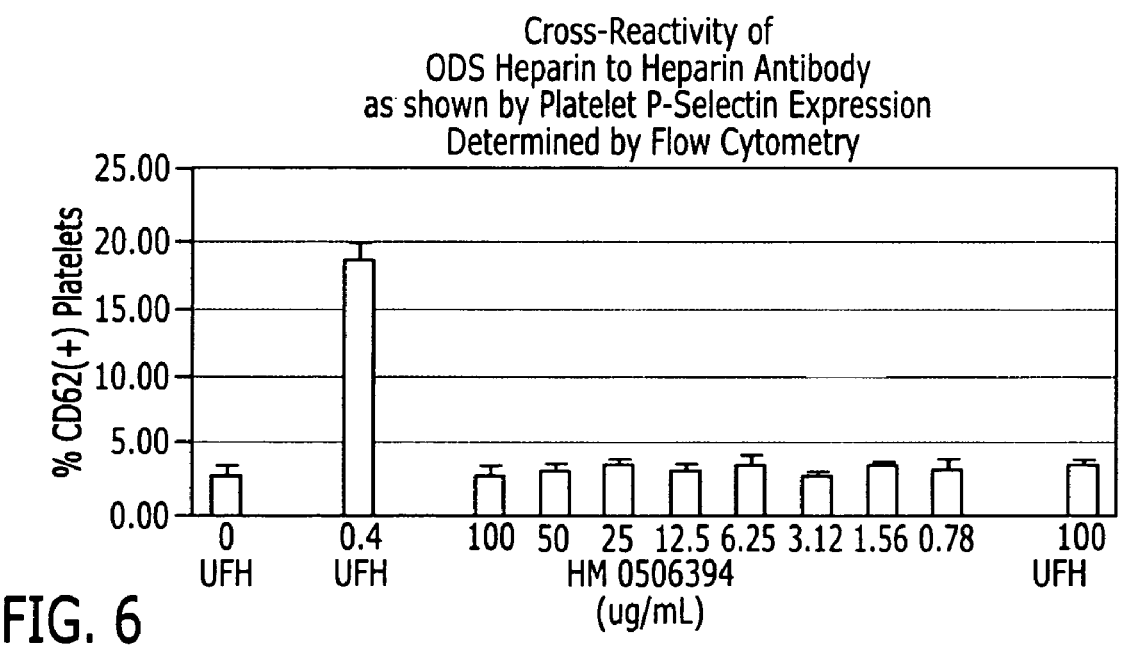
FIG. 6 shows cross-reactivity of the 2-O, 3-O desulfated heparin of this invention to heparin antibody as determined by expression of platelet surface P-selectin (CD62) quantitated by flow cytometry.

FIG. 6 shows that when unfractionated heparin at the usual therapeutic anticoagulant concentration of 0.4 µg/ml is incubated with platelets and HIT-antibody positive serum, there is prominent CD62 expression on the surface of approximately 20% of platelets. Saline controls incubations were characterized by low expression of CD62 (<2% of platelets). In contrast, 2-O desulfated heparin, studied at 0.78 to 100 µg/ml, did not increase CD62 expression levels above that observed in the saline control incubations. Furthermore, while 0.4 µg/ml unfractionated heparin produced substantial platelet microparticle formation, 2-O desulfated heparin at 0.78 to 100 µg/ml stimulated no level of platelet microparticle formation above that of the saline control incubations (<5% activity).

With a molecular weight of 10.5 kD and a degree of sulfation of about 1.0, ODS heparin would be predicted to elicit a HIT-like platelet activation response in the serotonin release and platelet microparticle formation assays (Greinacher A, et al., supra). Thus, it is surprising and not predictable from the prior art that 2-O desulfated heparin does not react with HIT antibody and PF4 to activate platelets and will not likely produce the HIT syndrome. This indicates that 2-O desulfated heparin is a safer therapeutic heparin analog for administration to patients for treatment of inflammatory and other conditions in need of heparin or heparin analog therapy, since 2-O desulfated heparin will not produce the serious and life-threatening HIT-2 syndrome.

More surprisingly, 2-O desulfated heparin actually suppresses platelet activation induced by HIT antibody and unfractionated heparin. For these amelioration experiments the 2-O desulfated heparin employed was manufactured by a larger commercial process detailed in Example III. The SRA and flow cytometry techniques, slightly modified from what was described above, were used to demonstrate this unique effect of the 2-O desulfated heparin.

Specifically, for the SRA platelet-rich plasma was collected, prepared and labeled as previously described. The test system mixture incorporated both 5 µl of 2-O desulfated heparin (0, 0.78, 1.56, 3.13, 6.25, 12.5, 25, 50 and 100 µg/ml final concentrations) and 5 µl of unfractionated heparin (either 0.1 or 0.5 U/ml final concentrations). The SRA was positive for amelioration of the unfractionated heparin induced platelet activation by the 2-O desulfated heparin if the UFH response was inhibited in the presence of 2-O desulfated heparin. Serotonin release <20% in the presence of UFH and 2-O desulfated heparin is considered complete amelioration.

Specifically, for the flow cytometric analyses, whole blood was collected and prepared as previously described. The test system mixture incorporated both 25 µl of 2-O desulfated heparin (0, 0.78, 1.56, 3.13, 6.25, 12.5, 25, 50 and 100 µg/ml final concentrations) and 25 µl of unfractionated heparin (either 0.1 or 0.5 U/ml final concentrations). Heparin without 2-O desulfated heparin was used as the control (0, 0.1, 0.5 and 100 U/ml UFH final concentrations). Any test agent such as 2-O desulfated heparin is considered positive for amelioration if the 0.1 and 0.5 U/ml UFH response is inhibited. Complete amelioration occurred if the platelet activation response was equivalent to that of the 100 U/ml UFH control (no test agent such as 2-O desulfated heparin present).

Figure 7:
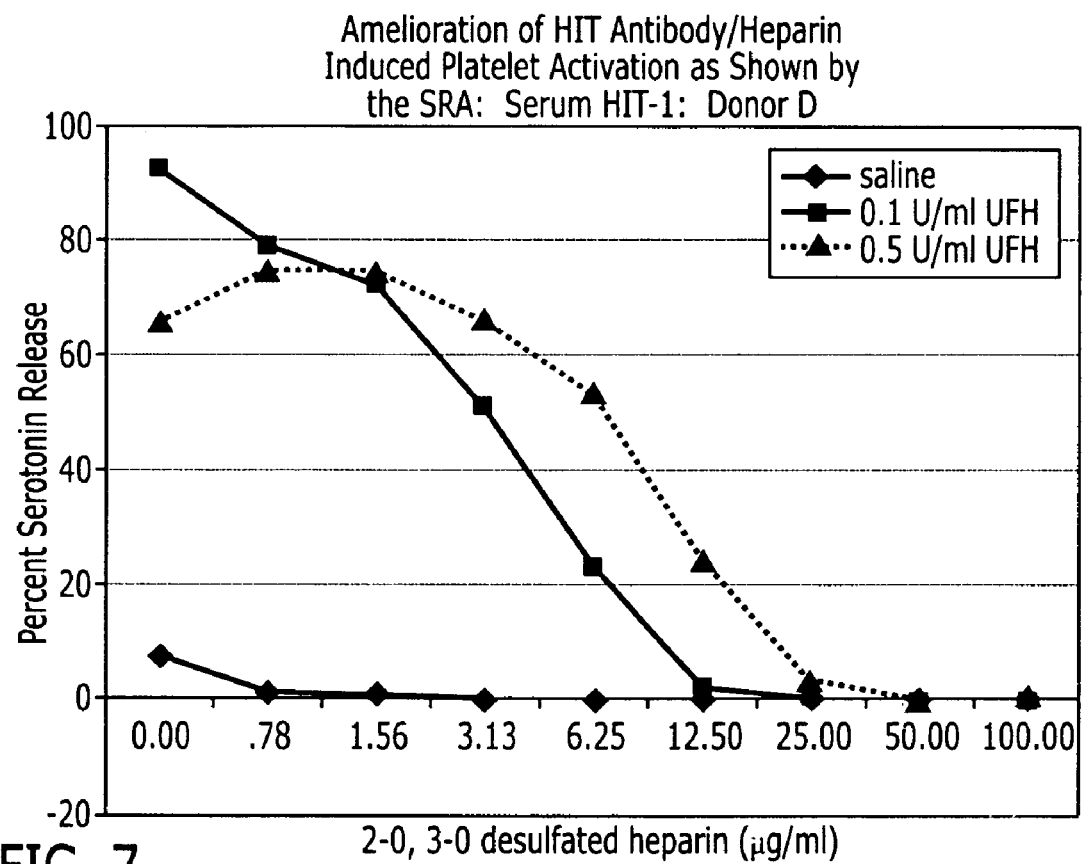
FIG. 7 is a graph showing that increasing concentrations of 2-O desulfated heparin, which is also 3-O desulfated, suppresses HIT-mediated platelet activation as shown by the release of platelet serotonin in response to adding 0.1 or 0.5 U/ml heparin to serum from a patient with HIT syndrome.
Figure 8:
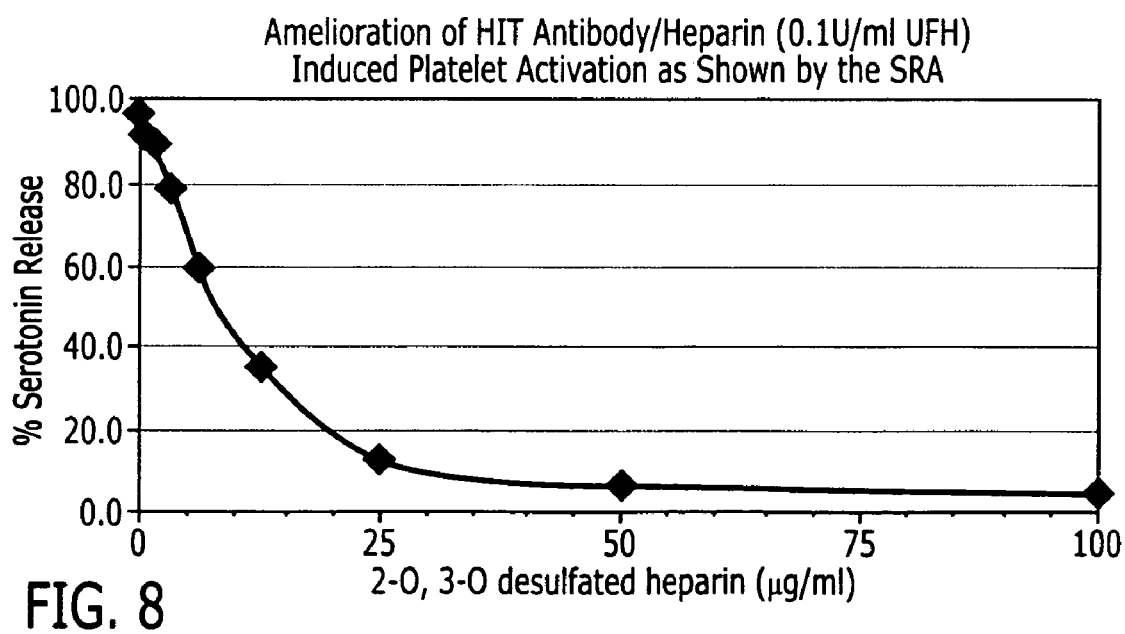
FIG. 8 is a graph showing mean results of experiments in which 2-O desulfated heparin, which is also 3-O desulfated, suppresses platelet activation as shown by serotonin release induced by 0.1 U/ml heparin (UFH) in the presence of sera from four patients with HIT.
Figure 9:
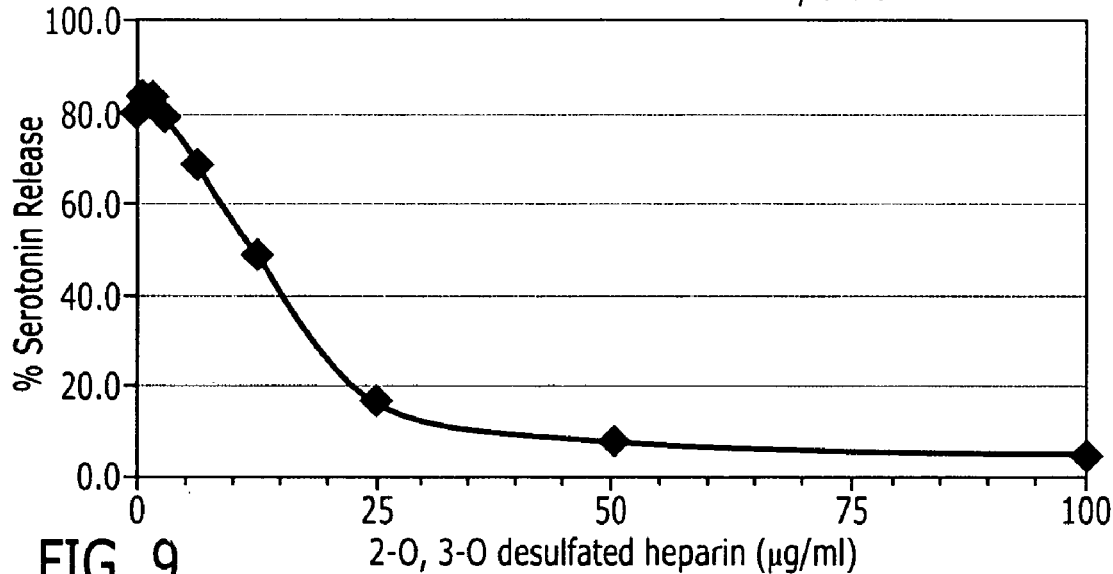
FIG. 9 shows a graph of the mean results of experiments in which 2-O desulfated heparin, which is also 3-O desulfated, suppresses platelet activation as shown by serotonin release induced by 0.5 U/ml heparin (UFH) in the presence of sera from four patients with HIT.

In the SRA, amelioration could be observed at concentrations of 2-O desulfated heparin, which is also 3-O desulfated, as low as 3.13 µg/ml. A higher concentration of the 2-O desulfated heparin (on average 6.25 µg/ml vs 3.13 µg/ml) was needed to initiate amelioration in the 0.5 U/ml UFH system compared to that needed in the 0.1 U/ml UFH system. Complete blockade of the HIT antibody/unfractionated heparin induced platelet activation was always obtained, but the concentrations of the 2-O desulfated heparin differed depending on the strength of the HIT antibody. FIG. 7 shows results of amelioration of SRA using serum from a typical HIT patient. In most patient sera, complete amelioration (defined as <20% serotonin release) was observed at 12.5 µg/ml and higher concentrations of 2-O desulfated heparin. Composite graphs of the data obtained in studying SRA inhibition with sera from four different HIT patients is shown using the 0.1 U/ml UFH system (FIG. 8) and the 0.5 U/ml UFH system (FIG. 9). It can be seen that amelioration is initiated at 6.25 µg/ml and complete amelioration of the SRA response is achieved with 25 µg/ml of 2-O desulfated heparin. No platelet activation was observed in the presence of 50 µg/ml of 2-O desulfated heparin. Due to the consistency of the data, the error bars (standard error of the mean; SEM) do not show.

Figure 10:
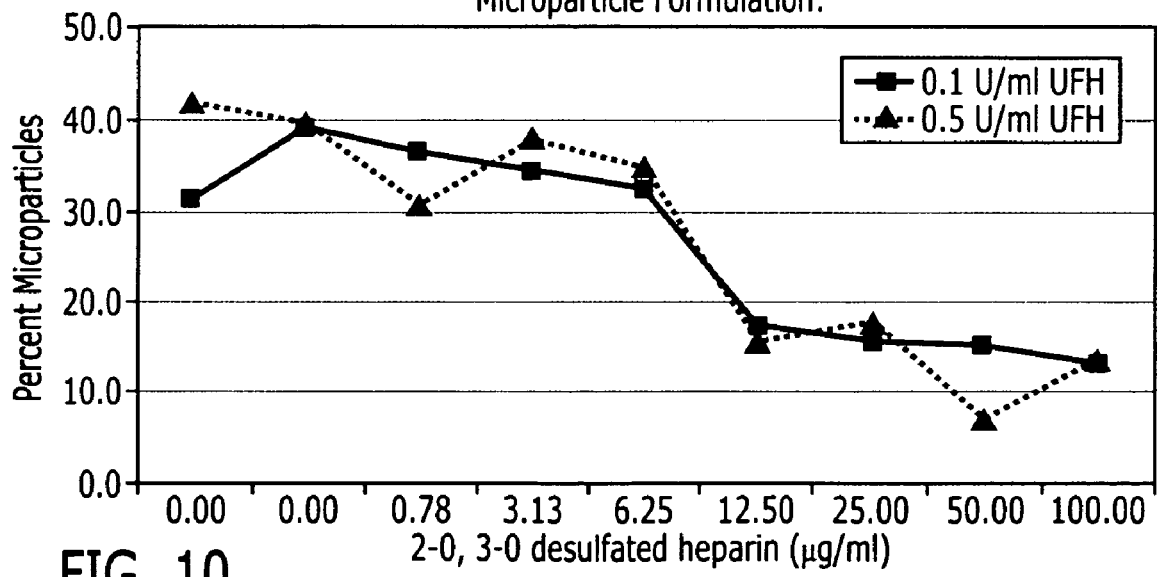
FIG. 10 is a graph showing that 2-O desulfated heparin, which is also 3-O desulfated, suppresses platelet microparticle formation when a HIT patient's serum is mixed with 0.1 U/ml or 0.5 U/ml heparin.
Figure 11:
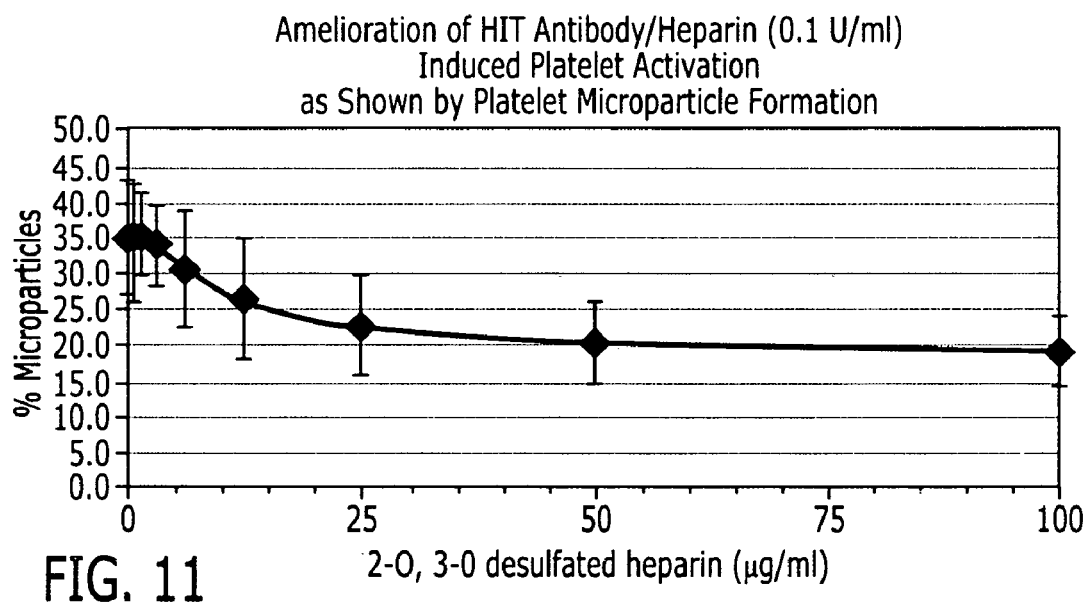
FIG. 11 is a graph showing mean results of experiments in which 2-O desulfated heparin, which is also 3-O desulfated, suppresses platelet microparticle formation when sera from each of four patients with HIT is mixed with 0.1 U/ml heparin.
Figure 12:
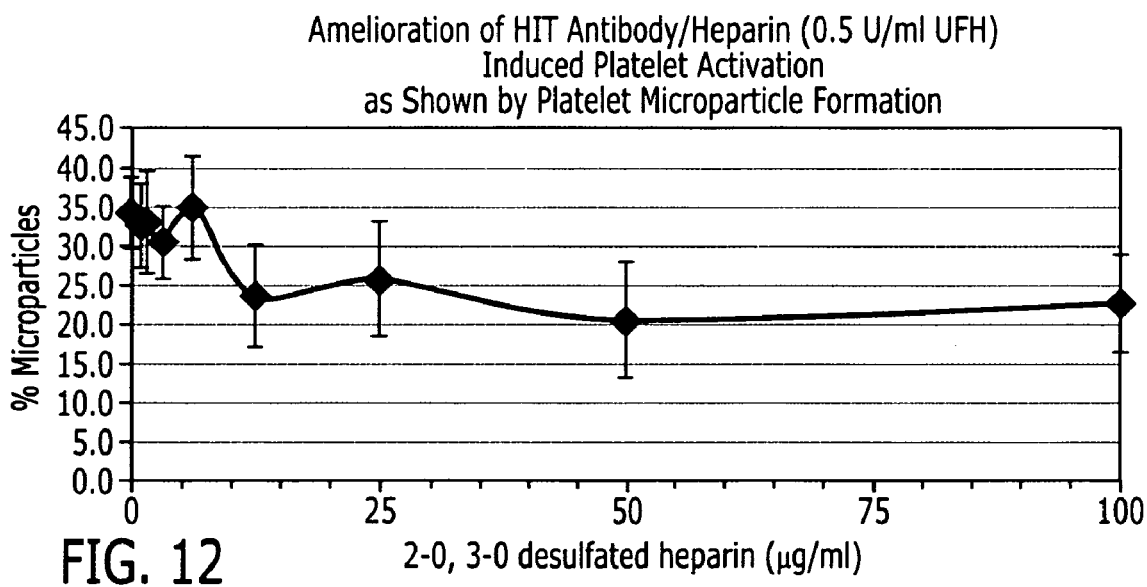
FIG. 12 is a graph showing mean results of experiments in which 2-O desulfated heparin, which is also 3-O desulfated, suppresses platelet microparticle formation when sera from each of four patients with HIT is mixed with 0.5 U/ml heparin.

Evaluation of 2-O desulfated heparin for amelioration of platelet activation induced by HIT antibodies/unfractionated heparin using the flow cytometric analysis of platelet microparticle formation and cell surface P-selectin expression as a measure of platelet activation showed an amelioration effect in all test systems (defined as inhibition of the response obtained with 0.1 and 0.5 U/ml UFH response when no 2-O desulfated heparin was present). For platelet microparticle formation, amelioration was observed at concentrations of 2-O desulfated heparin as low as 6.25 µg/ml. There was no remarkable difference between the amelioration response observed in the 0.1 U/ml and the 0.5 U/ml UFH systems. On average, amelioration was initiated at 6.25 µg/ml 2-O desulfated heparin. Complete blockade of the platelet activation was always obtained, but the concentrations of 2-O desulfated heparin differed depending on the strength of the HIT antibody. FIG. 10 shows results of amelioration of HIT/unfractionated heparin induced platelet microparticle formation using serum from a typical HIT patient. Composite graphs of the data obtained in studying inhibition of platelet microparticle formation with sera from four different HIT patients is shown using the 0.1 U/ml UFH system (FIG. 11) and the 0.5 U/ml UFH system (FIG. 12). Complete amelioration (defined as platelet activation response equivalent to that of the 100 U/ml UFH control when the test agent 2-O desulfated heparin was not present) was observed from 6.25 μg/ml and higher concentrations of 2-O desulfated heparin. Over average, a concentration of 50 μg/ml 2-O desulfated heparin was needed to achieve complete remission of platelet microparticle formation.

Figure 13:
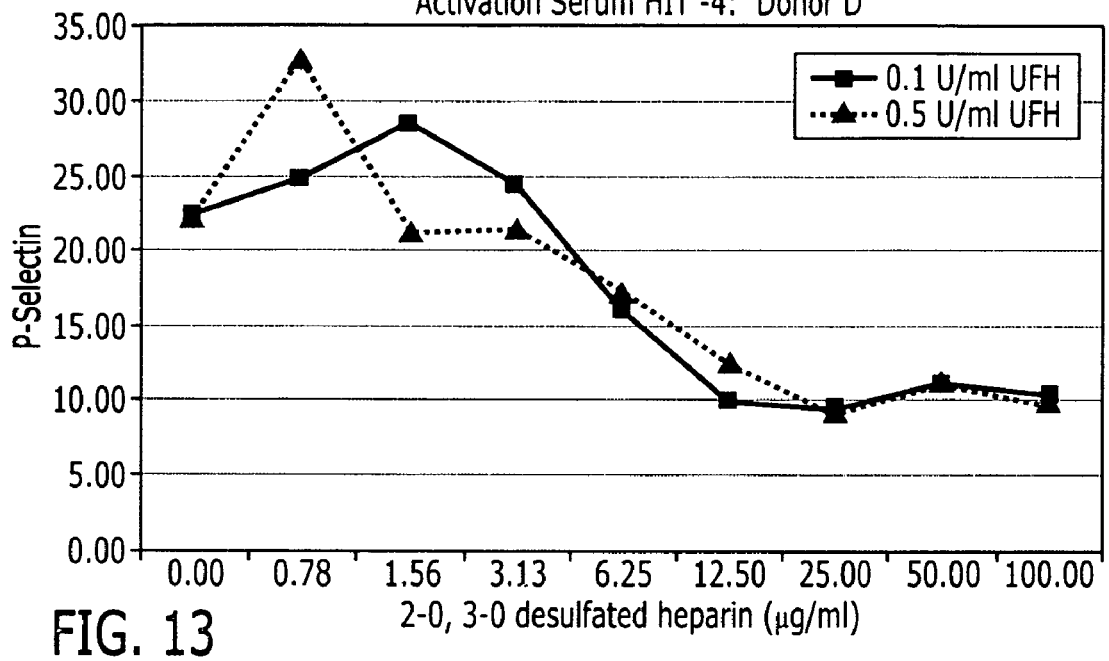
FIG. 13 is a graph showing that 2-O desulfated heparin, which is also 3-O desulfated, suppresses HIT-induced platelet activation measured by platelet surface expression of P-selectin (CD62)
Figure 14:
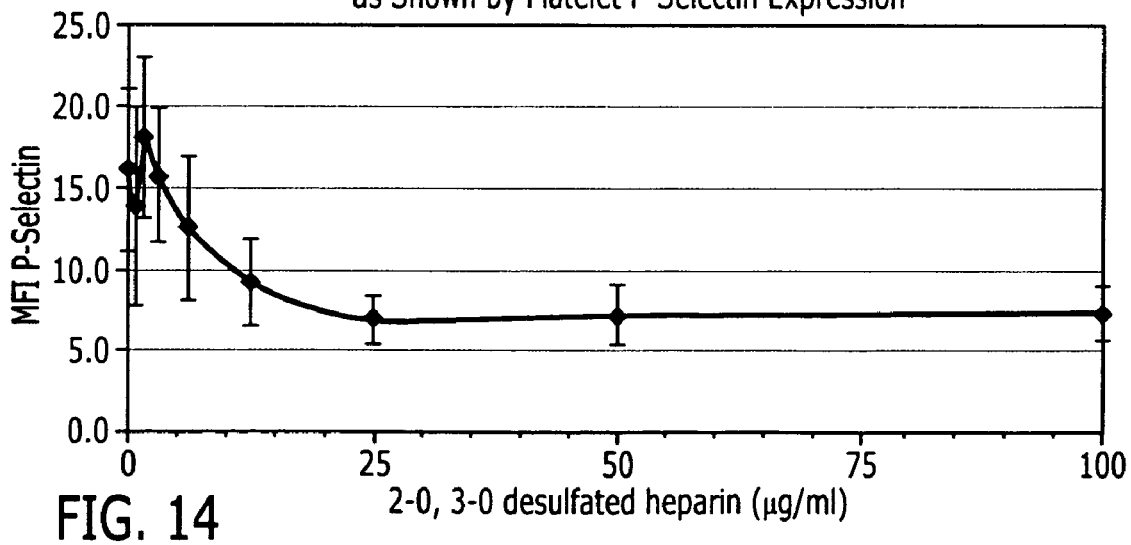
FIG. 14 is a graph showing mean results of experiments in which 2-O desulfated heparin, which is also 3-O desulfated, suppresses platelet surface expression of P-selectin (CD62) induced by HIT sera from each of four patients with HIT in the presence of 0.1 U/ml unfractionated heparin.
Figure 15:
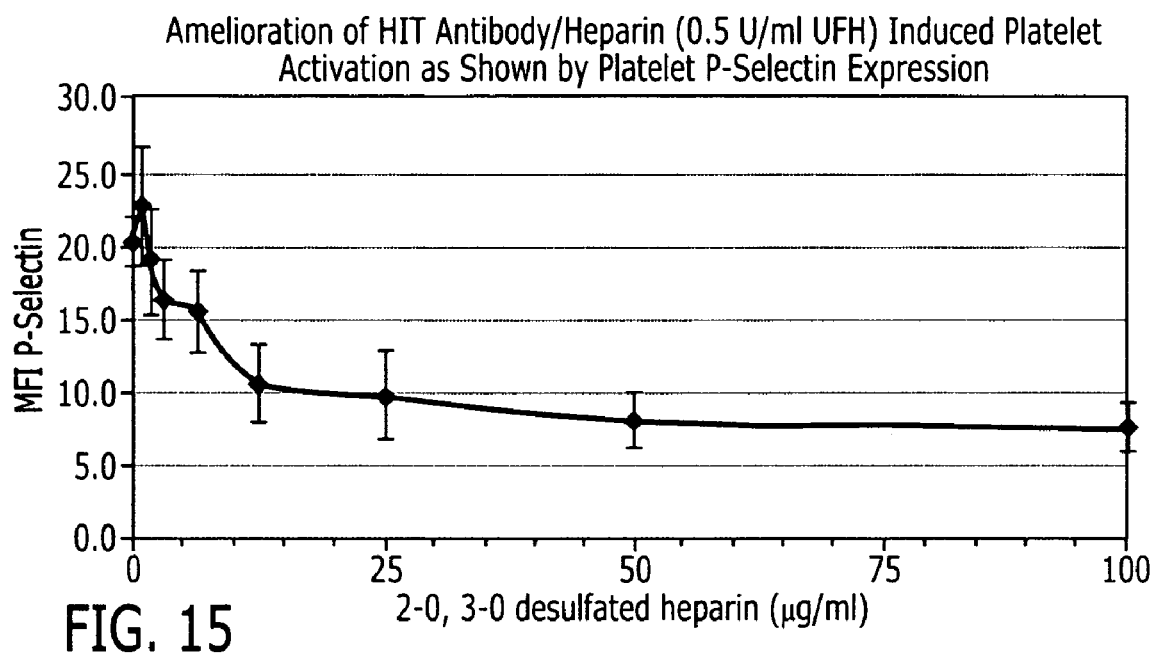
FIG. 15 is a graph showing mean results of experiments in which 2-O desulfated heparin, which is also 3-O desulfated, suppresses platelet surface expression of P-selectin (CD62) induced by HIT sera from each of four patients with HIT in the presence of 0.5 U/ml unfractionated heparin.

For P-selectin (CD62) expression, amelioration could be observed at concentrations of the 2-O desulfated heparin as low as 1.56 μg/ml. There was no remarkable difference between the amelioration response observed in the 0.1 U/ml and the 0.5 U/ml UFH systems. On average amelioration was initiated at 6.25 μg/ml 2-O desulfated heparin. Complete blockade of the platelet activation was always obtained, but the concentration of the 2-O desulfated heparin differed depending on the strength of the HIT antibody. FIG. 13 shows results of amelioration of HIT/unfractionated heparin induced platelet CD62 expression using serum from a typical HIT patient. Complete amelioration was observed from 6.25 μg/ml and higher concentrations of 2-O desulfated heparin. On average, a concentration of >25 μg/ml 2-O desulfated heparin was needed to achieve complete amelioration or suppression of platelet activation. Composite graphs of the data obtained in studying inhibition of platelet CD62 expression with sera from four different HIT patients is shown using the 0.1 U/ml UFH system (FIG. 14) and the 0.5 U/ml UFH system (FIG. 15). Amelioration is initiated at 6.25 μg/ml and complete amelioration of the platelet activation responses, measured by CD62 expression, is achieved with 50 μg/ml of 2-O desulfated heparin.

Example II

Intravenous Injection of 2-O Desulfated Heparin Produces Blood Levels Necessary for Complete Amelioration of Platelet Activation by Heparin in the Presence of a Heparin-Induced Thrombocytopenia Antibody To determine if levels of 2-O desulfated heparin reached sufficient concentration in vivo to suppress HIT-related platelet activation, three groups of beagle dogs (n=4 each) were injected with 2-O desulfated heparin (ODSH) produced as in Example III. Injections were given over 2 minutes in doses of O (saline control, group 1), 4 (group 2), 12 (group 3) and 24 mg/kg (group 4). Injections were performed 4 times daily for 10 days. On a daily basis, the total ODSH doses administered were 0, 16, 48 and 96 mg/kg. Whole blood was collected on study days 1, 2, 4, 6, and 8, at 15 minutes and 6 hours after the first injection of the day. Also, following the final ODSH injection, samples were collected at 15 minutes, and 1, 2, 4, 6 and 8 hours. All samples were collected in vacutainer tubes containing citrate as an anticoagulant.

The concentration of ODSH was measured by a potentiometric assay of developed for measurement of sulfated polysaccharides in biological fluids (see Ramamurthy N, Baliga N, Wakefield T W, Andrews P C, Yang V C, Myerhoff M E, Determination of low-molecular-weight heparins and their binding to protamine and a protamine analog using polyion-sensitive membrane electrodes. *Anal Biochem* 266: 116-124, 1999). Cylindrical polycation sensitive electrodes are prepared as described previously (see Ramamurthy N, Baliga N, Wahr J A, Schaller U, Yang V C, Meyerhoff M E, Improved protamine-sensitive membrane electrode for monitoring heparin concentrations in whole blood via protamine titration. *Clin Chem* 44:606-61, 1998). A cocktail with a composition of 1% (w/w) dinoylnaphthalene sulfonate, 49.5% (w/w) nitrophenyloctyl ether, and 49.5% (w/w) polyurethane M48 is prepared by dissolving components in distilled tetrahydrofuran (200 mg/ml). The resulting solution is dipcoated onto the rounded ends of sealed glass capillary tubes protruding slightly from 1 inch pieces of Tygon tubing (i.d.=1.3–1.5 mm). After dipcoating the solution 12 times at 15 minute intervals, the sensor bodies are dried overnight in a fume hood. On the day of use, the sensor bodies are soaked for at least one hour in PBS and the glass capillaries are carefully removed. The sensor body is then filled with PBS and a Ag/AgCl wire is inserted to complete the sensor. Sensors are used once and then discarded. Two sensors and a Ag/AgCl reference wire are connected to a VF-4 amplifier module (World Precision Instruments) that is interfaced to an NB-MIO analog/digital input/output board (National Instruments) in a Mac IIcx computer. The data is sampled at a 3 second interval and recorded with LabView 2.0 software. A titrant solution of 1 mg/ml protamine sulfate (clupeine form, Sigma) in PBS is prepared, and the titrant is delivered continuously via a syringe pump (Bioanalytical Systems). Titration end-points are computed using the Kolthoff method (See Sergeant E P, Potentiometry and potentiometric titrations. In: *Chemical Analysis* Kolthoff I M, Elwing P J, eds. 69:362-364, 1985), followed by application of a subtractive correction factor equivalent to the protamine concentration required to reach the end point of the calibration curve.

Figure 16:
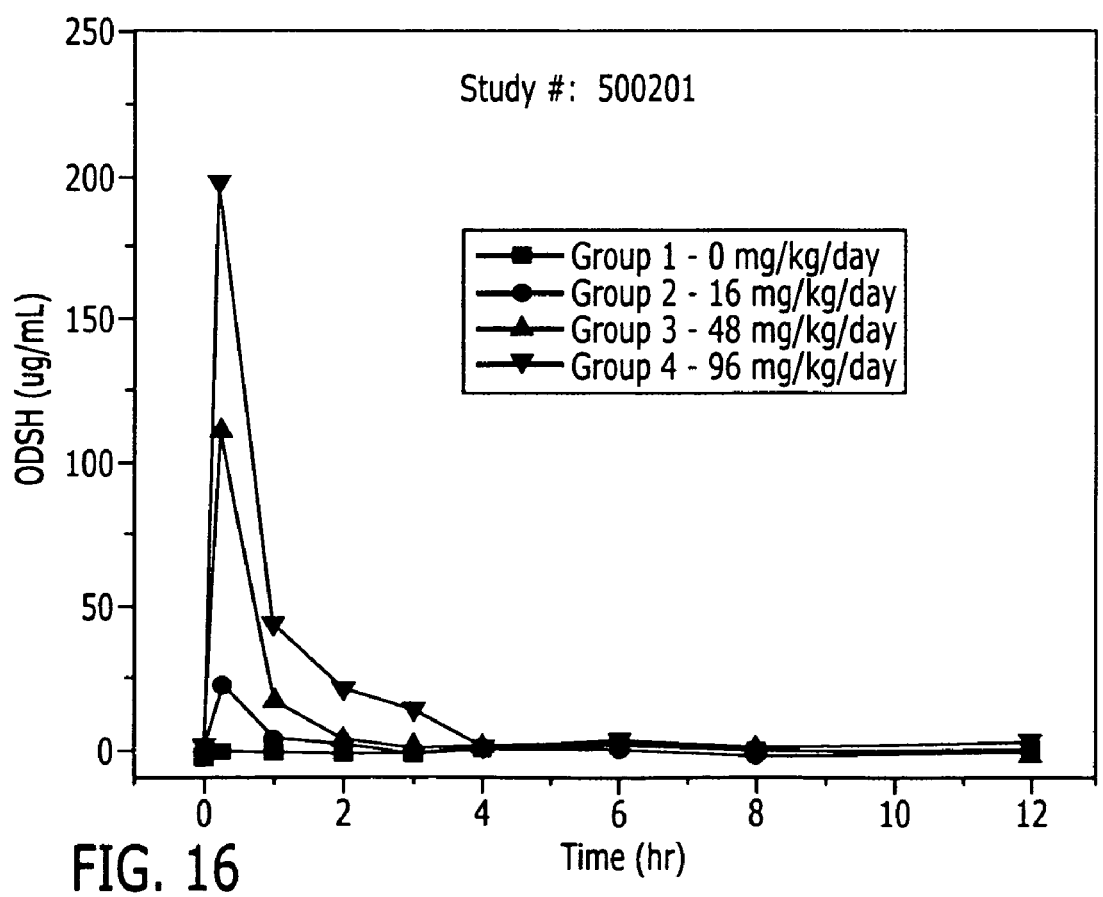
FIG. 16 is a graph showing blood concentrations of 2-O desulfated heparin, termed ODSH, after the final injection into male beagle dogs in doses of 4 mg/kg every 6 hours (16 mg/kg/day), 12 mg/kg every 6 hours (48 mg/kg/day), and 24 mg/kg every 6 hours (96 mg/kg/day) for 10 days.

FIG. 16 shows concentrations of ODSH in plasma at timed collection intervals for the three dose groups and control. The average concentrations at various time points is shown in Table 1 below:

TABLE 1

Mean ODS Heparin Concentrations after Injection

| | ODS Heparin concentration (μg/ml) | | | |
|---|---|---|---|---|
| Sample | 0 mg/kg/day | 16 mg/kg/day | 48 mg/kg/day | 160 mg/kg/day |
| 15 min post injection | −0.1 ± 0.4 | 14.0 ± 0.9 | 50.4 ± 18.9 | 237.9 ± 26.5 |
| 1 hr post injection | 2.3 ± 0.7 | 2.4 ± 0.7 | 14.6 ± 0.9 | 86.4 ± 12.1 |
| 3 hr post injection | 0.9 ± 0.7 | 0.6 ± 0.7 | 1.7 ± 0.7 | 17.2 ± 0.8 |
| 4 hr post injection | 1.0 ± 0.7 | 0.4 ± 0.7 | −0.1 ± 0.7 | 10.7 ± 0.8 |
| 6 hr post injection | 1.8 ± 0.7 | 0.4 ± 0.7 | 1.4 ± 0.7 | 5.7 ± 0.8 |
| 8 hr post injection | 0.9 ± 0.7 | 0.1 ± 0.7 | 0.9 ± 0.7 | 2.1 ± 0.8 |
| 12 hr post injection | 1.7 ± 0.7 | 2.3 ± 0.7 | 0.9 ± 0.7 | 3.7 ± 0.8 |

Compartmental modeling was performed using WinNonlin version 4.1. Tables 2 and 3 display the pharmacokinetic parameters AUC (area under the curve), K10-HL (terminal half life), Cmax (maximum concentration), CL (clearance), AUMC (area under the first moment curve), MRT (mean residence time), and Vss (volume of distribution at steady state) for each group respectively.

TABLE 2

Summary of pharmacokinetic parameters *

| Dose (mg/kg/day) | AUC (hr*ug/mL) | Vss (mL/kg) | CL (mL/hr/kg) | Cmax (ug/mL) | Half-life (hr) |
|---|---|---|---|---|---|
| 16 | 12.39 ± 1.92 | 127.23 ± 11.63 | 322.80 ± 49.98 | 23.28 ± 1.41 | 0.27 ± 0.06 |
| 48 | 59.90 ± 1.41 | 80.01 ± 1.11 | 200.35 ± 4.71 | 111.47 ± 1.03 | 0.28 ± 0.01 |
| 96 | 134.14 ± 10.96 | 97.39 ± 4.68 | 178.91 ± 14.63 | 197.60 ± 7.43 | 0.38 ± 0.04 |

* Estimates are ± SEM

TABLE 3

Compartmental Analysis Results

| Dose | Parameter | Units | Estimate | StdError | CV% |
|---|---|---|---|---|---|
| 16 | AUC | hr*ug/mL | 12.391491 | 1.916640 | 15.47 |
| 16 | K10-HL | hr | 0.273207 | 0.057834 | 21.17 |
| 16 | Cmax | ug/mL | 23.279975 | 1.406524 | 6.04 |
| 16 | CL | mL/hr/kg | 322.802142 | 49.978994 | 15.48 |
| 16 | AUMC | hr*hr*ug/mL | 6.433104 | 1.988164 | 30.91 |
| 16 | MRT | hr | 0.394155 | 0.083437 | 21.17 |
| 16 | Vss | mL/kg | 127.234069 | 11.627849 | 9.14 |
| 48 | AUC | hr*ug/mL | 59.895111 | 1.405766 | 2.35 |
| 48 | K10-HL | hr | 0.276820 | 0.008857 | 3.20 |
| 48 | Cmax | ug/mL | 111.469287 | 1.030526 | 0.92 |
| 48 | CL | mL/hr/kg | 200.350243 | 4.707016 | 2.35 |
| 48 | AUMC | hr*hr*ug/mL | 31.407007 | 1.471781 | 4.69 |
| 48 | MRT | hr | 0.399367 | 0.012778 | 3.20 |
| 48 | Vss | mL/kg | 80.013235 | 1.107527 | 1.38 |
| 96 | AUC | hr*ug/mL | 134.144991 | 10.958943 | 8.17 |
| 96 | K10-HL | hr | 0.377308 | 0.039373 | 10.44 |
| 96 | Cmax | ug/mL | 197.599118 | 7.433318 | 3.76 |
| 96 | CL | mL/hr/kg | 178.910892 | 14.630699 | 8.18 |
| 96 | AUMC | hr*hr*ug/mL | 89.788574 | 14.548574 | 16.20 |
| 96 | MRT | hr | 0.544340 | 0.056803 | 10.44 |
| 96 | Vss | mL/kg | 97.388309 | 4.684936 | 4.81 |

Levels of 2-O desulfated heparin are achieved that ameliorate all aspects of HIT platelet ctivation at injection doses of 4 mg/kg (16 mg/kg/day) and greater. With a load and infusion rate of approximately one-fifth the loading dose every hour, steady state levels are likely to be achievable in all cases.

Example III

Commercially Feasible Production of 2-O Desulfated Heparin that is Nonanticoagulant and Inhibitory for Human Leukocyte Elastase Nonanticoagulant 2-O desulfated heparin can be produced in even larger, more commercially feasible quantities. USP porcine intestinal heparin is purchased from a reliable commercial vendor such as Scientific Protein Laboratories (SPL), Wanaukee, Wis. It is dissolved at room temperature (20±5° C.) to make a 5% (weight/volume) solution in deionized water. As a reducing step, 1% (weight/volume) sodium borohydride is added and agitated for 2 hours. The solution is then allowed to stand at room temperature for 15 hours. The pH of the solution is then alkalinized to greater than 13 by addition of 50% sodium hydroxide. The alkalinized solution is agitated for 2-3 hours. This alkalinized solution is then loaded onto the trays of a commercial lyophilizer and frozen by cooling to −40° C. A vacuum is applied to the lyophilizer and the frozen solution is lyophilized to dryness. The lyophilized product is dissolved in cold (<10° C.) water to achieve a 5% solution. The pH is adjusted to about 6.0 by slow addition of hydrochloric acid with stirring, taking care to prevent the solution temperature at <15° C. The solution is then dialyzed with at least 10 volumes of water or subjected to ultrafiltration to remove excess salts and reducing agent. To the dialyzed solution, an amount of 2% sodium chloride (weight/volume) is added. The 2-O desulfated heparin product is then precipitated using one volume of hysol (denatured ethanol). After the precipitation has settled for about 16 hours, the supernatant is siphoned off. The precipitate is re-dissolved in water to a 10% (weight/volume) solution. The pH is adjusted to 5-6 using hydrochloric acid or sodium hydroxide, the solution is filtered through a 0.2 µ filter capsule into a clean container. The filtered solution is then lyophilized to dryness. The resulting product can be made by this method with yields up to 1.5 kg. The final product is a 2-O desulfated heparin with a pH of 6.4, a USP anticoagulant activity of about 6 U/mg, and an anti-Xa anticoagulant activity of 1.9 U/mg. The product is free of microbial and endotoxin contamination, and the boron content measured by ICP-AES is <5 ppm. This 2-O desulfated heparin been tested for in rats and dogs at doses as high as 160 mg/kg daily for up to 10 days, with no substantial toxicity.

The resulting 2-O desulfated heparin is useful for inhibiting the enzymatic activity of human leukocyte elastase. This is tested by methods detailed in U.S. Pat. Nos. 5,668,188; 5,912,237; and 6,489,311, incorporated herein by reference. Briefly, the inhibition of human leukocyte elastase (HLE) was measured by incubating a constant amount of HLE (100 pmol) with a equimolar amount of 2-O desulfated heparin (I/E ratio 1:1) for 30 minutes at 25° C. in 500 µL of Hepes buffer (0.125 M, 0.125% Triton X-100, pH 7.5) diluted to the final volume of 900 µL. The remaining enzyme activity is measured by adding 100 µL of 3 mM N-Suc-Ala-Ala-Val-nitroanalide (Sigma Chemical, St. Louis, Mo., made in dimethylsulfoxide). The rate of change in absorbance of the proteolytically released chromogen 4-nitroanline is monitored at 405 nm. The percentage inhibition is calculated based upon enzyme activity without inhibitor. The 2-O desulfated heparin produced by above methods inhibits HLE >90% at a 1:1 enzyme to inhibitor molar ratio.

The bulk product can be formulated into convenient unit dose vials of 50 mg/ml. This is accomplished by adding 2-O desulfated heparin to USP sterile water for injection to make a 6.5% (weight/weight) solution. Sodium chloride and sterile water for injection are added to adjust the final osmolality to 280-300 mOsm, and the pH is adjusted to 7.1-7.3 using 1 N hydrochloric acid or sodium hydroxide as needed. The solution is filtered and transferred to a sterile fill Class 100 area where unit dose glass vials are filled with 21 ml solution each, sealed, crimped and labeled.

Example IV

Figure 17:
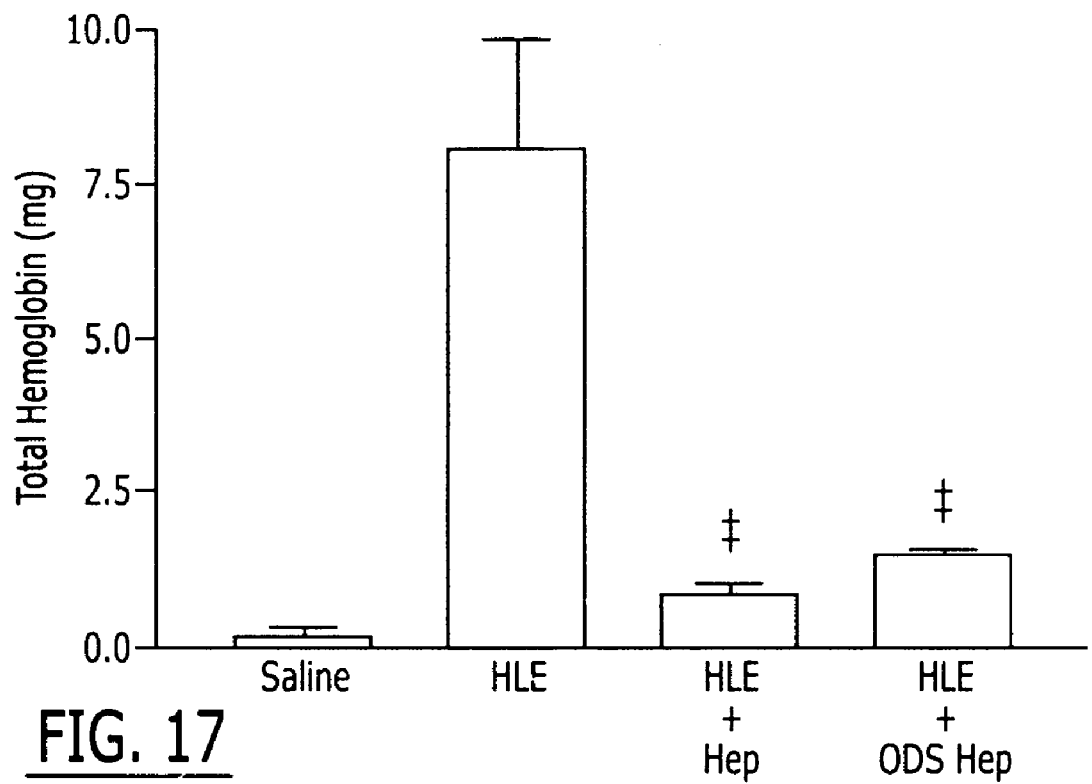
FIG. 17 shows a graph of the hemoglobin content measured in the bronchoalveolar lavage fluid 24 hours after administration of saline (control), human leukocyte elastase (HLE), HLE plus heparin, and HLE plus ODS heparin.
Figure 18:
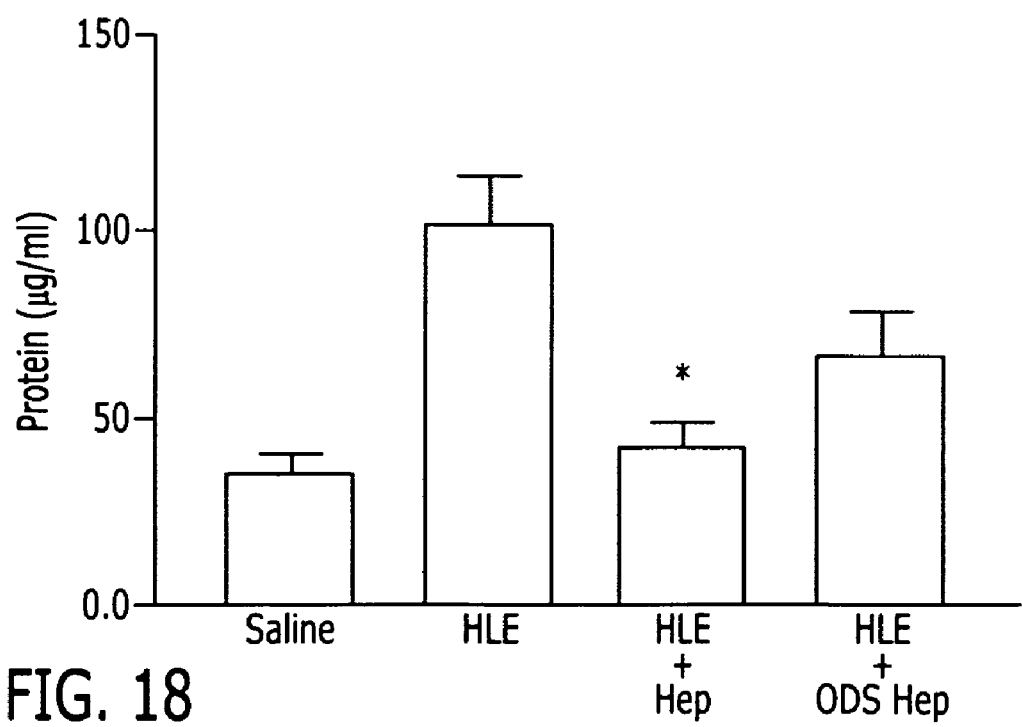
FIG. 18 shows a graph of the concentration of protein in the bronchoalveolar lavage fluid 24 hours after administration of saline (control), human leukocyte elastase (HLE), HLE plus heparin, and HLE plus ODS heparin.
Figure 19:
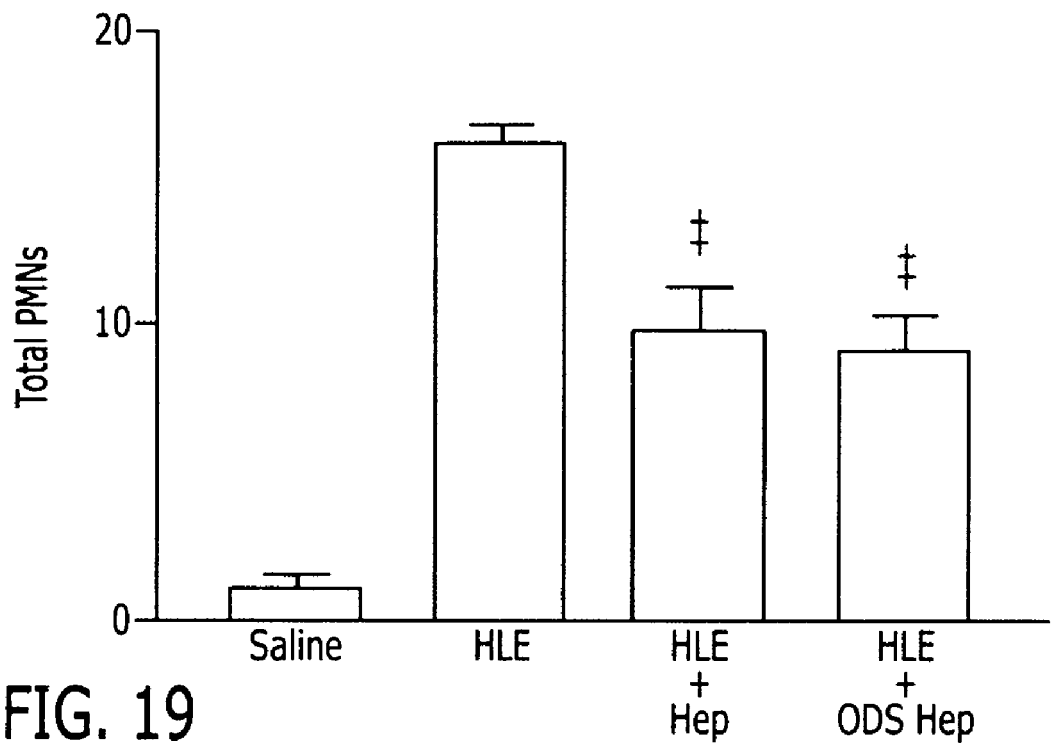
FIG. 19 shows a graph of the number of polymorphonuclear leukocyte (PMN) cells in the bronchoalveolar lavage fluid 24 hours after administration of saline (control), human leukocyte elastase (HLE), HLE plus heparin, and HLE plus ODS heparin.

Prevention of Lung Injury from Human Leukocyte Elastase with 2-O Desulfated Heparin The ability of 2-O desulfated heparin to prevent human leukocyte elastase (HLE)-mediated lung injury was assessed in female golden Syrian hamsters (Harlan Industries, Indianapolis, Ind.) weighing 90 to 110 g. Phenobarbital-anesthetized hamsters were injected intratracheally with 0.25 ml sterile 0.9% saline (NS), 0.25 ml NS containing HLE (100 µg) or 0.25 ml NS containing 500 µg of heparin (Sigma) or 2-O desulfated heparin according to Example I followed by 0.25 ml NS with HLE. Animals were killed by exsanguinations 24 hours after treatment. The throat was opened and lungs dissected en bloc. The trachea was cannulated with polyethylene tubing and lavaged with five sequential aliquots of 3 ml NS. Lavage fluid was centrifuged at 200×g for 10 minutes. The resulting cell pellet was re-suspended in 1 ml Hank's balanced salt solution (HBSS) for performing cell count and differential. The supernatant was assayed for protein and hemoglobin as indices of acute injury. The results are shown in FIGS. 17-19. Both heparin and 2-O desulfated heparin were potent inhibitors of elastase induced injury in vivo.

The 2-O desulfated heparin from Example I has been tested for toxicity. Other sulfated polysaccharide inhibitors of elastase such as dextran sulfate, produced hemorrhage into lung air sacs (alveolar hemorrhage) when injected into rats intratracheally in doses as low as 0.5 mg/kg. The 2-O desulfated heparin from Example I produced no alveolar hemorrhage in rats even in at intratracheal doses of 10 mg/kg.

The 2-O desulfated heparin from Example I can be used in humans to treat elastase mediated lung injury. As an example, for treatment of a patient with cystic fibrosis, a dose that provides a 5:1 ratio of inhibitor to protease is prepared and administered as an aerosol. In a patient producing 50 ml of sputum per day and producing average amounts of leukocyte elastase in the sputum, this dose can be about 25-250 mg of 2-O desulfated heparin administered by nebulizer over a course of 24 hours. Elastase levels in the patient's sputum can be monitored during treatment. The advantage of 2-O desulfated heparin over unmodified heparin in treating human elastase mediated lung injury is that 2-O desulfated heparin is nonanticoagulant and is less likely to cause lung hemorrhage in patients such as cystic fibrosis who are prone to coughing up blood (hemoptysis). Another substantial advantage of 2-O desulfated heparin over unmodified heparin is that 2-O desulfated heparin does not react with HIT antibodies, so there is no risk of life-threatening heparin-induced thrombocytopenia and thrombosis.

Example V

Materials Used in Subsequent Examples

Acetylcholine chloride, the calcium ionophore A23187, sodium nitroprusside, and indomethacin (Sigma, St. Louis, Mo.), and U-46619 (Upjohn, Kalamazoo, Mich.) were used in concentrations determined by Sato et al (see Sato H, et al. L arginine inhibits neutrophil adherence and coronary artery dysfunction. *Cardiovasc Res* 31:63-72, 1996). Grade I-A heparin sodium salt from porcine intestinal mucosa (Sigma) was resuspended with Krebs-Henseliet (KH) buffer and administered as an intravenous bolus (3 mg/kg to dogs). Nonanticoagulant 2-O desulfated nonanticoagulant heparin (ODS-HEP) was synthesized according to Example I and according to Fryer et al (see Fryer A, et al., Selective O-desulfation produces nonanticoagulant heparin that retains pharmacologic activity in the lung. *J Pharmacol Exp Therap* 282:208-219, 1997) from unfractionated porcine intestinal heparin 170 USP/mg anticoagulant activity and 150 U/mg anti-Xa activity. While 1.0 mg/ml of unmodified heparin inhibited 91±2% of the lysis of human red cells by canine plasma, ODS-HEP reduced erythrocyte lysis only by 4±2% at 1.0 mg/ml. ODS-HEP was resuspended in Krebs Heinseleit (K-H) buffer and administered as an intravenous bolus (3 mg/kg to dogs; 6 mg/kg to rats, with 100 µg/ml added to K-H perfusate for isolated hearts).

Example VI

In Vivo Ischemia-Reperfusion Studies Performed

Surgical Procedure

All animals were handled in compliance with the Guide for the Care and Use of Laboratory Animals, published by the National Institutes of Health (NIH Publication No. 85-23, revised 1985). The Institutional Animal Care and Use Committees of Emory University and Carolinas Medical Center approved the study protocols.

Twenty-four heartworm-free adult dogs of either sex were anesthetized with sodium pentobarbital (20 mg/kg) and endotracheally intubated. Anesthesia was supplemented with fentanyl citrate (0.3 µg/kg/min) and diazepam (0.03 µg/kg/min) administered intravenously as needed to maintain deep anesthesia. Each dog was ventilated with a volume-cycled respirator using oxygen-enriched room air. A rectal temperature probe was inserted to measure core body temperature. The right femoral artery and vein were cannulated with polyethylene catheters for arterial blood sampling and for intravenous access, respectively. Serial arterial blood gases were measured to maintain the arterial oxygen tension greater than 100 mmHg. Arterial carbon dioxide tension was maintained between 30 and 40 mmHg, and arterial pH was maintained between 7.35 and 7.45 by adjustment of the ventilatory rate, and acidemia was counteracted with intravenous sodium bicarbonate.

After median sternotomy, the superior and inferior vena cava were looped with umbilical tapes and the heart suspended using a pericardial cradle. Millar catheter-tipped pressure transducers (Millar Instruments, Houston, Tex.) were placed in the proximal aorta and in the left ventricular cavity to measure aortic and left ventricular pressure, respectively. A polyethylene catheter was inserted into the left atrium for colored microsphere injection. A one centimeter portion of the left anterior descending (LAD) coronary artery distal to the first diagonal branch was dissected and loosely encircled with a 2-O silk suture. A pair of opposing ultrasonic crystals were placed intramyocardially within the proposed ischemic area at risk within the left anterior descending coronary artery distribution, and were used to assess regional function within the area at risk (see Jordan J E, et al., Adenosine A2 receptor activation attenuates reperfusion injury by inhibiting neutrophil accumulation, superoxide generation and coronary adherence. *J Pharmacol Exp Therap* 280; 301-309, 1997).

Experimental Protocol

Dogs were randomized to one of three groups (n=8 in each group): 1) Control (saline), 2) unmodified heparin (HEP, 3 mg/kg) and 3) modified heparin (ODS-HEP, 3 mg/kg). The LAD was occluded for 90 min producing ischemia and then released for four hours of reperfusion. Each pharmaceutical agent (saline, HEP, ODS-HEP) was infused as an intravenous bolus 10 minutes prior to initiation of reperfusion and at 90 and 180 minutes during reperfusion. Analog hemodynamic and cardiodyamic data were sampled by a personal computer using an analog-todigital converter (Data Translation, Marlboro, Mass.). Hemodynamic and cardiodynamic data were averaged from no fewer than 10 cardiac cycles. Percent systolic shortening, segmental work, and the characteristics of segmental stiffness described by exponential curve-fitting analysis were determined as described previously in J.E. Jordan, et al., supra. Activated clotting time (ACT, in seconds) was measured throughout the experiment using the Hemochron 401 Whole Blood Coagulation System (International Technidyne, Edison, N.J.). Arterial blood creatine kinase activity was analyzed using a kit from Sigma Diagnostics and expressed as international units per gram of protein. The experiment was terminated with a bolus of intravenous sodium pentobarbital (100 mg/kg). The heart was immediately excised for further analysis and placed into ice-cold Krebs-Henseleit (K-H) buffer of the following composition (mmol/L): 118 NaCl, 4.7 KCl, 1.2 $KH_2PO_4$, 1.2 $MgSO_4$ 7 $H_2O$, 12.5 $CaCl_2$ 2 $H_2O$, 12.5 $NaHCO_3$, and 11 glucose at pH 7.4.

Determination of Area at Risk, Infarct Size and Regional Myocardial Blood Flow

After post-experimental excision of the heart, the myocardial area at risk and infarct size were determined by J. E. Jordan, et al., supra, using Unisperse pigment exclusion and 1% triphenyltetrazolium chloride, respectively. The area at risk (AAR) and infarct size were calculated gravimetrically as previously described (J. E. Jordan, et al. supra). Regional myocardial blood flow in the ischemic-reperfused and non-ischemic myocardium were obtained by spectrophotometric analyses of dye-release colored microspheres (Triton Technology, San Diego, Calif.). Left atrial injections of microspheres and reference blood sampling were performed at baseline, at the end of 90 minutes of ischemia, and at 15 minutes and four hours of reperfusion.

Measurement of Myocardial Neutrophil Accumulation

Tissue samples of 0.4 g were taken from the non-ischemic zone and from the nonnecrotic and necrotic regions of the area at risk for spectrophotometric analysis of myeloperoxidase (MPO) activity (δ absorbance/minute), for assessment of neutrophil (PMN) accumulation in myocardium, as described in Jordan J E, et al., supra.

PMN Adherence to Post-Experimental Coronary Artery Endothelium

PMN adherence to post-experimental coronary arteries was used as a bioassay of basal endothelial function. Canine PMNs were isolated from arterial blood and fluorescent labeled as previously described (see Zhao, Z-Q, Sato H, Williams M W, Fernandez A Z, Vinten-Johansen J, Adenosine A2-receptor activation inhibits neutrophil-mediated injury to coronary endothelium. Am J Physiol Heart Circ Physiol 271:H1456-H1464, 1996). After excision of the heart, ischemic-reperfused LAD and non-ischemic left circumflex (LCx) segments were isolated, cut into 3-mm segments, opened to expose the endothelium while being submerged in ice-cold K-H buffer, and then placed in dishes containing K-H buffer at 37° C. After unstimulated, fluorescent-labeled PMNs (6×106 cells/dish) were incubated with post-experimental segments for 15 minutes, the coronary segments were washed of non-adherent PMNs, mounted on glass slides, and adherent PMNs were counted under epifluorescence microscopy (490-nm excitation, 504-nm emission), as described previously (see Thourani V H, Nakamura N, Durarter I G, Bufkin B L, Zhao Z-Q, Jordan J E, Shearer S T, Guyton R A, Vinten-Johansen J, Ischemic preconditioning attenuates postischemic coronary artery endothelial dysfunction in a model of minimally invasive direct coronary artery bypass grafting. J Thorac Cardiovasc Suirg 117:838-389, 1999).

Agonist-Stimulated Macrovascular Relaxation

Agonist-stimulated vasoreactivity in epicardial macrovessels from ischemic (LAD) and nonischemic (Lcx) was studied using the organ chamber technique (see Zhao, Z-Q, et al., supra). Indomethacin (10 μmol/L) was used to inhibit prostaglandin release. Coronary rings were precontracted with the thromboxane A2 mimetic U-46619 (5 nmol/L). Endothelial function was assessed by comparing the vasorelaxation responses to incremental concentrations of acetylcholine (1-686 μmol/L) and A23187 (1-191 μmol/L), whereas smooth muscle function was assessed with sodium nitroprusside (1-381 μmol/L).

Example VII

In Vitro Ischemia-Reperfusion Studies Performed

PMN Degranulation

Supernatant MPO activity was measured as the product of canine PMN degranulation using the method by Ely as modified by Jordan J E, Thourani V H, Auchampach J A, Robinson J A, Wang N-P, Vinten-Johansen J, $A_3$ adenosine receptor activation attenuates neutrophil function and neutrophil-mediated reperfusion injury. Am J Physiol Heart Circ Physiol 277:H1895-H1905, 1999. Canine PMNs (20×106 cells/ml) were incubated in the presence or absence of ODS heparin and stimulated to degranulate with platelet activating factor (PAF, 10 μmol/L) and cytochalasin B (5 μg/ml). MPO activity in supernatants was assayed spectophotometrically.

PMN Adherence to Normal Coronary Artery Endothelium.

Adherence of PMNs to normal canine epicardial arteries was assessed using coronary segments and PMNs from normal animals. Unstimulated PMNs and coronary artery segments prepared and labeled as described for adherence studies were coincubated in the presence or absence of heparin or ODS heparin. After PAF (100 nmol/L) stimulation for 15 min, adherent PMNs were counted as outlined earlier.

Experiments with Human Umbilical Vein Endothelial Cells (HUVEC)

Primary HUVECs were isolated according to the method of Jaffe, et al. (Jaffe E A, Nachmann R L, Becker C G. Culture of human endothelial cells derived from umbilical veins: identification by morphological criteria. J Clin Invest 52:2745-2750, 1973), cultured on coverslips using endothelial cell growth medium (Clonetics) and tested for expression of von Willebrand's factor. HUVECs were washed twice with PBS and incubated in Neuman/Tytell medium alone for 24 h, followed by incubation with lipopolysaccharide (1 μg/ml) plus 10-20 ng/ml TNFα for 2 hours, or in heparin or ODS-HEP (200 μg/ml) for 4 hours with the addition of lipopolysaccharide and TNFα after 2 hours. HWECs were fixed for 20 minutes on ice with 4% paraformaldehyde in CEB (10 mmol/L Tris-HCl, pH 7.9, 60 mmol/L KCl, 1 mmol/L EDTA, 1 mmol/L dithiothreitol) with protease inhibitors, PI (1 mmol/L Pefabloc, 50 μg/ml antipain, 1 μg/ml leupeptin, 1 μg/ml pepstatin, 40 μg/ml bestatin, 3 μg/ml E-64, and 100 μg/ml chymostatin), permeabilized for 2 minutes with 0.1%

NP40 in CEB/PI, washed once with cold CEB and fixed as before for 10 minutes. Coverslips were incubated in 3% $H_2O_2$ for 30 minutes to suppress peroxidase, washed three times in cold PBS, blocked for 2 hours with 2% bovine serum albumin (BSA) in PBS on ice and incubated overnight at 4° C. with 1 µg/ml of anti-p65 antibody (Santa Cruz Biotechnology, Santa Cruz, Calif.) diluted in 0.1% BSA/PBS. Unbound anti-p65 was washed away with 2% BSA/PBS and bound antibody was incubated with biotinylated swine anti-rabbit immunoglobulin (1:1000) in 0.1% BSA/PBS for 45 minutes on ice, followed by 3 washes with 2% BSA/PBS. Coverslips were then incubated with streptavidin biotin peroxidase at room temperature for 1 hour, washed again, incubated in 0.03% wt/vol 3-3' diaminobenzidine with 0.003% $H_2O_2$ until a brown reaction product could be seen, counterstained with eosin and viewed under light microscopy.

Electrophoretic mobility shift assays (EMSAs) were also used to study the translocation of NF-κB from the cytoplasm to the nucleus. Nuclear proteins were obtained from HUVEC as described by Digman, et al. (Digman J D, Lebovitz R M, Roeder R G. Accurate transcription initiation by RNA polymerase II in a soluble extract from isolated mammalian nuclei. *Nucleic Acid Res* 11: 1475-1481, 1983) with the addition of the following proteinase inhibitors: 1 mmol/L phenylmethylsulfonyl fluoride, 1 µg/ml pepstatin A, 0.5 µg/ml chymostain, 1 µg/ml antipain, 1 µg/ml leupeptin and 4 µg/ml aprotinin. The double stranded oligonucleotide DNA probe (Santa Cruz) of the NF-κB consensus sequence AGT-TGAGGGGACTTTCCCAGGC [SEQ ID NO 1] was 5'OH end-labeled with [$\gamma^{32}$P]ATP using polynucleotide kinase. Free radionucleotide was removed using a Sephadex G-25 column. The probe (0.5 ng) was incubated with 10 µg HUVEC nuclear protein (Bio-Rad method) in 20 µl buffer containing a final concentration of 10 mmol/L HEPES, pH 7.5, 50 mmol/L KCl, 5 mmol/L $MgCl_2$, 1 mmol/L dithiothreitol, 1 mmol/L EDTA and 5% glycerol, plus 5 µg of poly (dI-dC) to reduce nonspecific binding. Incubations were carried out at room temperature for 20 minutes. Reactions were electrophoresed at 14 V/cm for 1.5-2.0 hours on a 6% nondenaturing polyacrylamide gel in 0.5×TBE (45 mmol/L Tris borate, 25 mmol/L boric acid, 1 mmol/L EDTA) at 4° C., and autoradiographed at –80° C.

Experiments with Isolated Perfused Rat Hearts

Male Sprague-Dawley rats (300-400 g) were anesthetized with sodium pentobarbital (40 mg/kg, i.p.), and the hearts were quickly excised and perfused in a Langendorff apparatus as previously described (Watts J A, Maiorano P C, Trace amounts of albumin protect against ischemia and reperfusion injury in isolated rat hearts. *J Mol Cell Cardiol* 31:1653-1662, 1999) with modified Krebs-Henseleit bicarbonate buffer (KHB), consisting of (in mmol/L): 118 NaCl, 4.7 KCl, 1.2 $KH_2PO_4$, 1.2 $MgSO_4$ 7 $H_2O$, 3.0 $CaCl_2$ 2 $H_2O$ (yielding 2.5 mmol/L free $Ca^{2+}$ in the presence of EDTA), 0.5 EDTA, 11 dextrose, and 25 $NaCHO_3$. Three groups were studied: 1) nonischemic control hearts were perfused 45 minutes; 2) ischemic-reperfused hearts were subjected to 15 minutes warm global ischemia and 15 minutes reperfusion; and 3) ODS heparin hearts from rats injected with 6 mg/mg ODS heparin i.v. 120 minutes before heart excision were subjected to 15 minutes each of global ischemia and reperfusion, with 100 µg/ml ODS heparin in perfusion buffer. After perfusion, ventricles were frozen with Wollenberger clamps precooled in liquid $N_2$, and pulverized under liquid $N_2$. Nuclear proteins were immediately isolated from frozen myocardial powders by the method of Li et al. (Li C, Browder W, Kao R, Early activation of transcription factor NF-κB during ischemia in perfused rat heart. *Am J Physiol Heart Circ Physiol* 276: H543-H552, 1999). EMSAs were performed using 15 µg of nuclear protein (Pierce protein assay) in each binding reaction. Competition experiments were performed by incubation of nuclear proteins with 10× unlabeled NF-κB or cyclic-AMP responsive element oligonucleotides (CRE, AGAGATTGC-CTGACGTCAGAGAGCTAG) [SEQ ID NO 2] for 5 minutes prior to addition of $^{32}$P-labeled NF-κB probe. Supershift assays were performed by adding 0.5 µg of antibodies to p65 and p50 components of NF-κB (Santa Cruz) to the binding reaction after labeled probe. Reactions were electrophoresed at 100 V for 2 hours at room temperature on a 5% nondenaturing polyacrylamide gel in 0.5 × TGE (120 mmol/L glycine, 1 mmol/L EDTA, 25 mmol/L Tris, pH 8.5) and autoradiographed.

Statistical Analysis

The data were analyzed by one-way analysis of variance or repeated measures two-way analysis of variance for analysis of group, time and group-time interactions. If significant interactions were found, Tukey's or Student-Newman-Keuls post hoc multiple comparisons tests were applied to locate the sources of differences. Differences in the densities of the p65-containing NF-κB gel band between treated and untreated ischemic reperfused rat hearts were compared using the t test. A $p<0.05$ was considered significant, and values are expressed as mean±standard error of the mean (SEM).

Example VIII

2-O Desulfated Heparin Reduces Infarct Size

Figure 20:
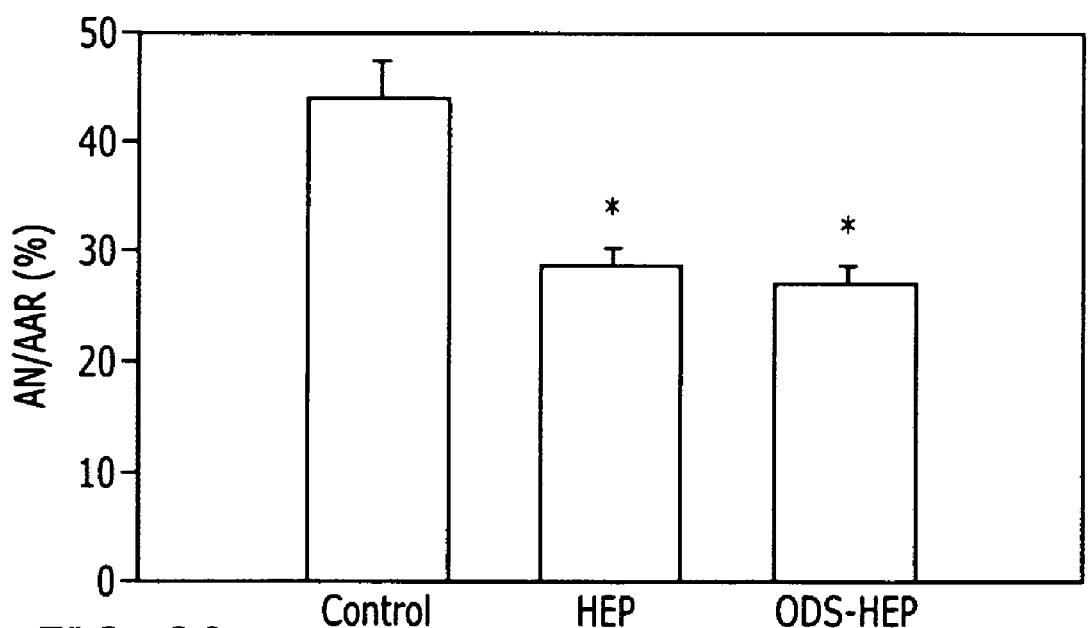
FIG. 20 is a graph showing that heparin and ODS desulfated heparin reduce plasma infarct size (ratio of area necrosis/area at risk, or AN/AAR)

Using the procedures described above, heparin and 2-O desulfated heparin significantly reduced myocardial infarct size. As shown in FIG. 20, the area at risk (AAR) is expressed as a percentage of the left ventricle (LV) at risk for infarction. The infarct size (area of necrosis, AN) is expressed as a percentage of the area at risk (AAR). *$p<0.05$ versus Control. Heparin (HEP) or 2-O desulfated heparin (ODS-HEP) treatment decreased infarct size (area of necrosis, AN), expressed as a percentage of the area at risk (AN/AAR), by 35% and 38%, respectively, compared to Controls. There was no statistical difference in size of infarcts between the HEP and ODS-HEP groups, and the area at risk from LAD occlusion, expressed as a percentage of the left ventricular mass (AAR/LV), was comparable among groups.

Figure 21:
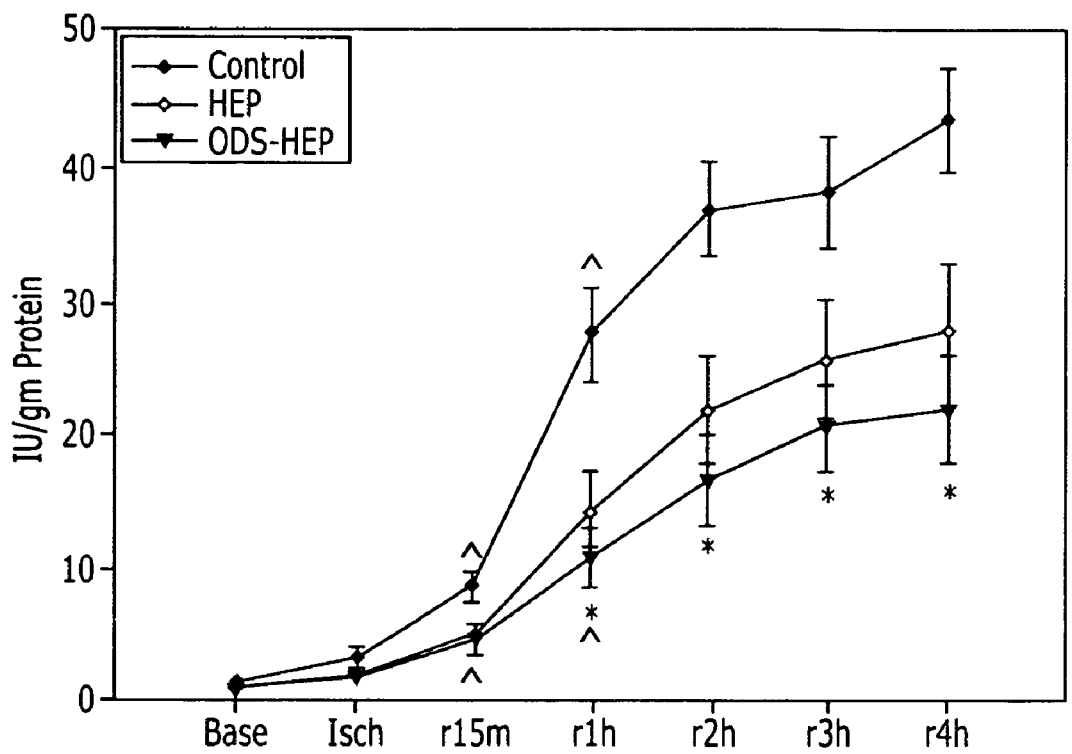
FIG. 21 demonstrates that heparin and ODS heparin reduce plasma creatine kinase activity after myocardial infarction.

As shown in FIG. 21, plasma creatine kinase (CK) activity was used to confirm histologic measurement of infarct size during the time course of the experiment. *$p<0.05$ HEP and OPSHEP versus Control. There were no significant differences in plasma CK activity at baseline among groups and no increases in CK activity after regional ischemia. Hearts in the Control group showed a steep rise in CK activity within the initial hour of reperfusion, which was significantly reduced by HEP or ODS-HEP treatment, consistent with the smaller infarct sizes in these groups (CK after 4 hour reperfusion=43.4±3.7 for Control; 27.6±5.3 for HEP; and 21.9±4.0 international units/g protein for ODS-HEP).

Despite their favorable effects on infarct size, HEP and ODS-HEP produced no significant changes in myocardial blood flow. Subendocardial blood flow in the ischemic-reperfused LAD coronary artery region was statistically comparable among the three groups at baseline. Regional myocardial blood flow was studied in the area at risk (AAR) which is in the distribution of the ischemic-reperfused left anterior descending (LAD) coronary artery. There were also no differences in regional myocardial blood flow in the distribution of the nonischemic-reperfused left circumflex (LCx) coronary artery. Transmural blood flow in the area at risk was significantly decreased during ischemia, with no group differences. All groups showed a comparable hyperemic response in the area at risk at 15 minutes of reperfusion, after which blood flow was diminished to similar levels in all groups by four hours. In the non-ischemic-reperfused LCx coronary artery region, transmural blood flow was comparable in all groups throughout the protocol.

Differences in infarct size were also not from hemodynamic or cardiodynamic differences. Hemodynamics at baseline and during ischemia and reperfusion were comparable among groups (data not shown). Heart rate was significantly increased during ischemia and reperfusion in all animals, and left ventricular end diastolic pressure was comparably elevated during ischemia in all three groups. Following ischemia, hearts in all groups demonstrated dyskinesis in the area at risk. All hearts showed poor recovery of percent systolic shortening throughout the four hours of reperfusion (−6±2% for Control hearts; −7±3% for HEP treated hearts; and −6±4% for ODS-HEP treated hearts at 4 hr reperfusion), and diastolic stiffness (as measured by the valueless β-coefficient) increased following ischemia to comparable levels in all groups (from 0.2±0.05 at baseline to 0.7±0.1 units after 4 hr reperfusion in Control hearts; from 0.2±0.04 at baseline to 1.0±0.2 units after 4 hr reperfusion in HEP treated hearts; from 0.2±0.04 at baseline to 0.5±0.2 units after 4 hr reperfusion in ODS-HEP treated hearts).

Example IX

Figure 22:
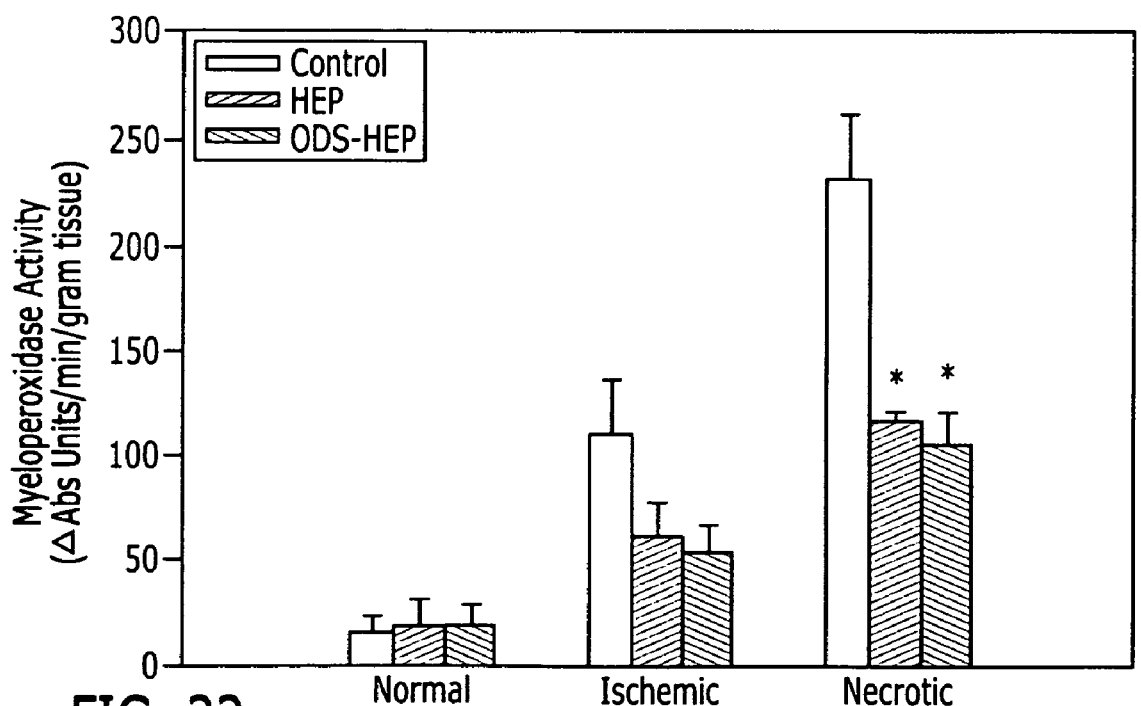
FIG. 22 demonstrates that heparin and ODS heparin reduce influx of polymorphonuclear leukocytes (PMNs) into myocardium after myocardial infarction, measured by the activity of the PMN specific enzyme myeloperoxidase in myocardial tissue.

Heparin and 2-O Desulfated Heparin Reduce PMN Accumulation in Reperfused Myocardium Using the procedures described above, heparin and 2-O desulfated heparin were found to reduce PMN accumulation in reperfused myocardium. PMN influx is a major mechanism underlying lethal reperfusion injury. Treatment with HEP or ODS-HEP significantly reduced myeloperoxidase (MPO) activity in necrotic myocardium by 50% compared to the Control group as shown in FIG. 22. In FIG. 22 myeloperoxiase activity, an index of PMN accumulation, is shown in normal ischemic, and necrotic myocardial tissue samples from each group. *$p<0.05$ HEP and ODS-HEP versus Control. PMN accumulation within normal myocardium was low and comparable among Control, HEP and ODS-HEP groups (16±8, 18±11, and 18±8δ absorbance units/minute, respectively). HEP and ODS-HEP both decreased MPO activity in the non-necrotic area at risk, but these changes did not achieve significance ($p>0.10$).

Example X

2-O Desulfated Heparin Does Not Produce Anticoagulation

Figure 23:
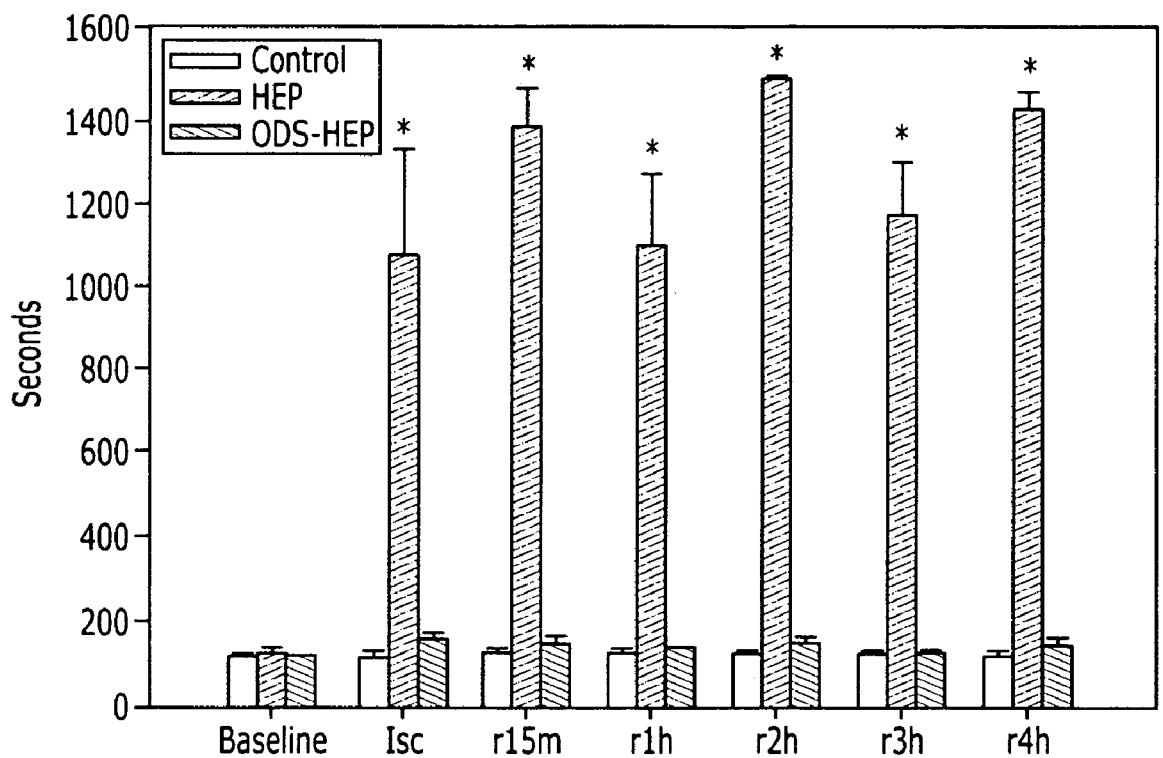
FIG. 23 shows that ODS heparin does not produce anticoagulation in vivo, measured by the activated clotting time (ACT), but that identical amounts of heparin produce profound anticoagulation, measured by prolongation of the ACT.

Despite reducing infarct size, ODS-HEP did not produce anticoagulation. As shown in FIG. 23, systemic whole blood anticoagulation was studied using the activated clotting time, measured in seconds. *$p<0.05$ HEP versus other groups. At four hours of reperfusion, activated clotting time (ACT) was increased greater than ten-fold after HEP treatment compared with Control (1425±38 seconds versus 123±10 seconds, respectively). In contrast, ACT in the ODS-HEP group (145±10 seconds) was not different from Controls (123±10 seconds, p=0.768). Thus, ODS-HEP was able to affect the same benefits as HEP without anticoagulation.

Example XI

Figure 24:
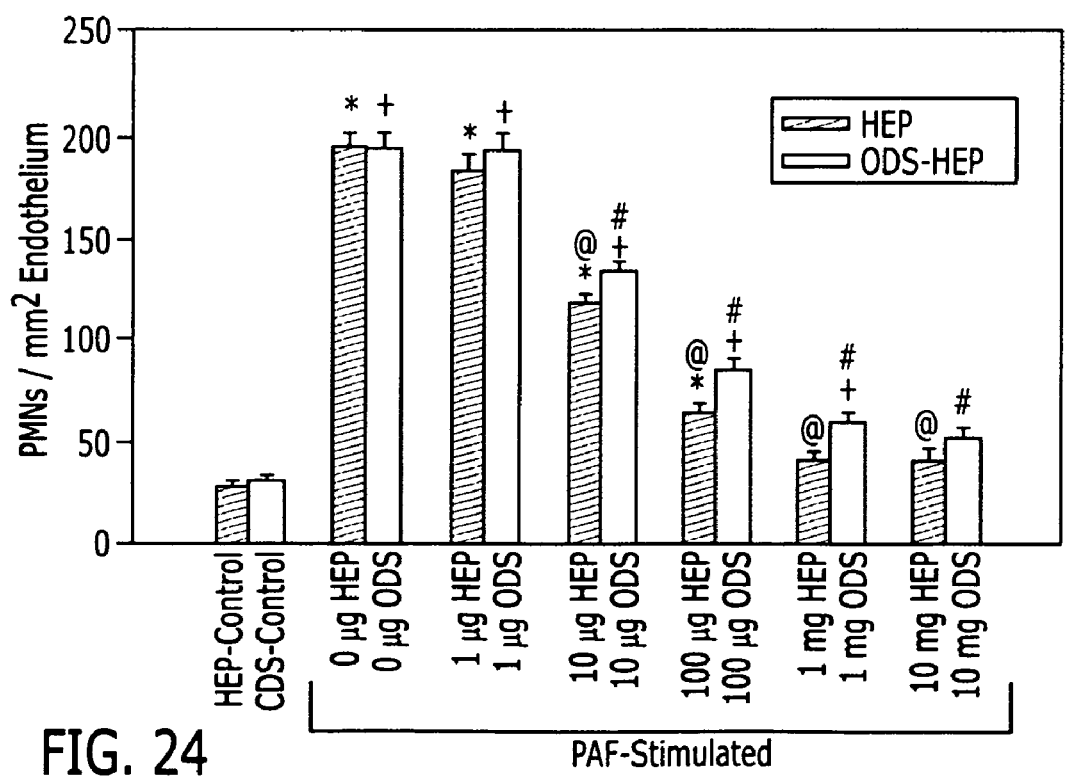
FIG. 24 demonstrates that heparin and ODS heparin block PMN adherence to normal coronary artery endothelium in vitro.

Heparin and 2-O Desulfated Heparin Reduce Neutrophil Adherence and Endothelial Dysfunction in Coronary Arteries This example shows that heparin and 2-O, 3-O desulfated heparin reduce neutrophil and endothelial dysfunction in coronary arteries. ODS-HEP did not significantly reduce PAF stimulated PMN degranulation, suggesting that ODS-HEP has little direct effect on PMN activity. However, PAF-stimulated PMN attachment to coronary endothelium was significantly reduced by both HEP and ODS-HEP in a dose-dependent manner (FIG. 24). Neutrophil adherence to normal coronary endothelium was stimulated by 100 nM platelet activating factor (PAF) added to medium and was inhibited in a dose-dependent manner by HEP or ODS-HEP. *$p<0.05$ HEP group versus HEP control, @ $p<0.05$ HEP group versus 0 mg HEP group, +$p<0.05$ ODS-HEP versus ODS control and #$p<0.05$ ODS-HEP versus 0 mg ODS group. Inhibition of PMN adherence to PAF-stimulated coronary endothelium was charge dependent, as suggested by reversal of the inhibiting effects of the polyanions HEP or ODS-HEP on attachment by the polycation protamine (PMNs/mm$^2$ endothelium=66±3 with 100 μg/ml HEP versus 180±8 with HEP+1 mg/ml protamine; 86±4 with 100 μg/ml ODS-HEP vs 136±4 with ODSHEP+1 mg/ml protamine; $p<0.05$ for both).

Figure 25:
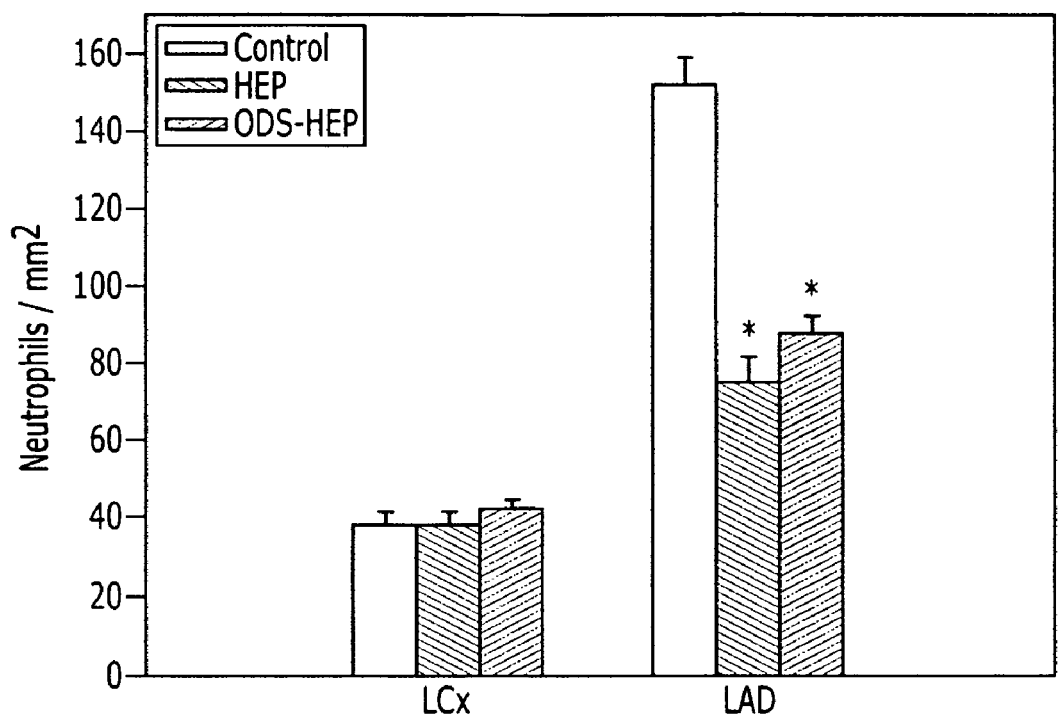
FIG. 25 illustrates that heparin and ODS heparin reduce PMN adherence to post-experimental coronary artery endothelium.

HEP and ODS-HEP also reduced PMN adherence to ischemic-reperfused coronary endothelium in vivo. The bar graph in FIG. 25 shows that PMN adherence to the ischemic-reperfused LAD coronary artery was increased by 300% in the untreated Control group compared to the non-ischemic-reperfused LCx artery. Neutrophil (PMN) adherence to the coronary endothelium was quantitated as the number of adherent PMNs/mm$^2$ of coronary endothelium. LCx=the non-ischemic-reperfused left circumflex coronary artery, LAD=the ischemic-reperfused left anterior descending coronary artery. *$p<0.05$ HEP and ODS-HEP versus LAD control. HEP or ODS-HEP reduced PMN adherence to the ischemic-reperfused LAD by 51 and 42%, respectively, compared to untreated Controls (FIG. 25).

HEP and ODS-HEP also preserved receptor-mediated vasodilator responses of coronary endothelium following ischemia and reperfusion. To quantify agonist-stimulated endothelial dysfunction in epicardial coronary arteries, the vascular response to incremental concentrations of the vasodilators acetylcholine (endothelial-dependent; receptor-dependent), A23187 (endothelial-dependent; receptor-independent), and sodium nitroprusside (direct smooth muscle) in post-ischemic coronary vascular ring preparations was studied.

Figure 26:
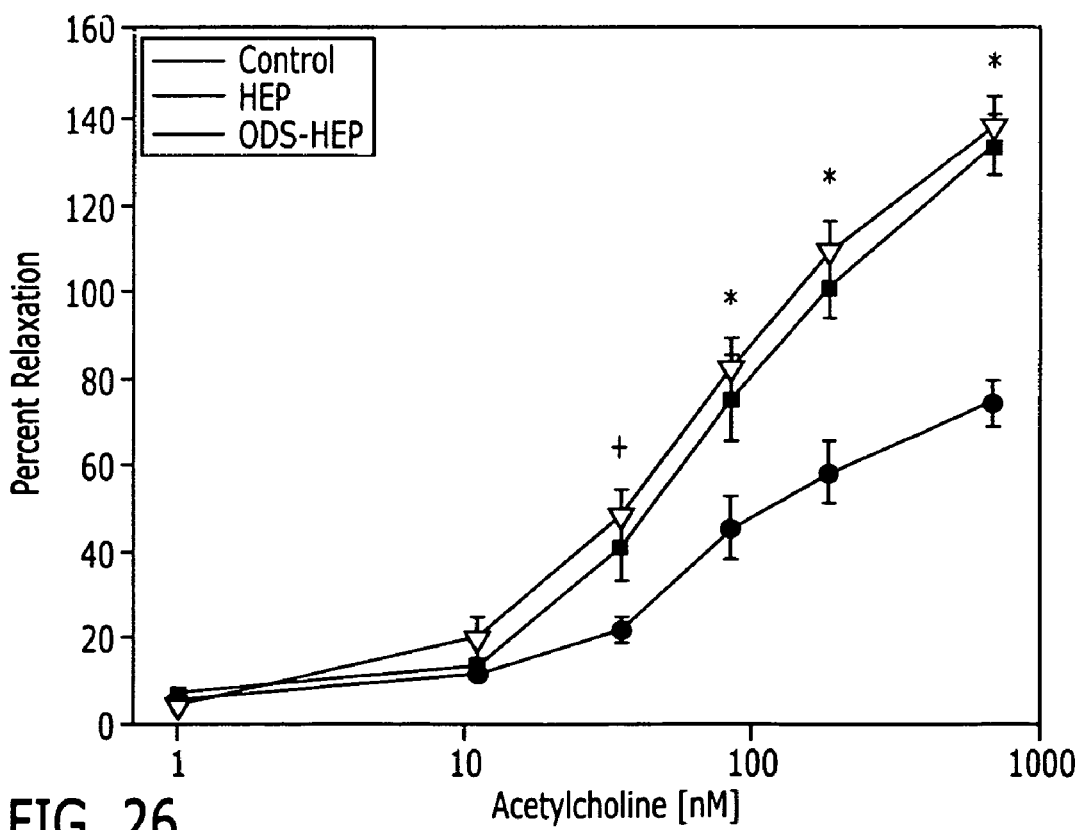
FIG. 26 shows that heparin and ODS heparin preserve the vasodilator function of ischemic-reperfused coronary arteries.
Figure 27A:
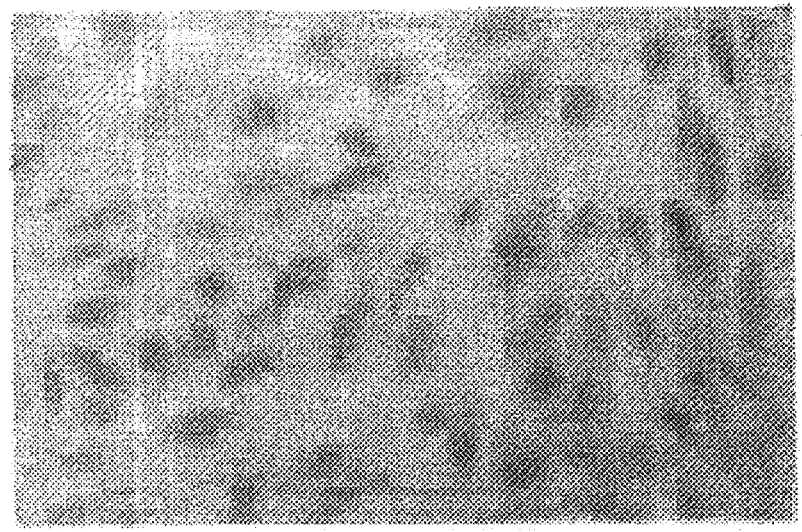
FIG. 27A demonstrates that nuclear factor-κ B (NF-κB, brown stained) is normally present in the cytoplasm of unstimulated human umbilical vein endothelial cells (HUVECs)
Figure 27B:
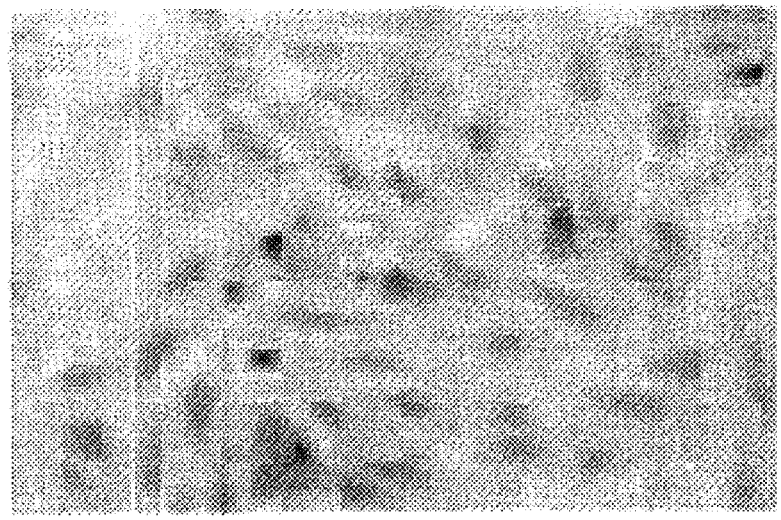
FIG. 27B shows that HUVECs stimulated with tumor necrosis factor α (TNFα) without addition of heparin. Some, but not all nuclei now stain positive for anti-p65, corresponding to trans.
Figure 27C:
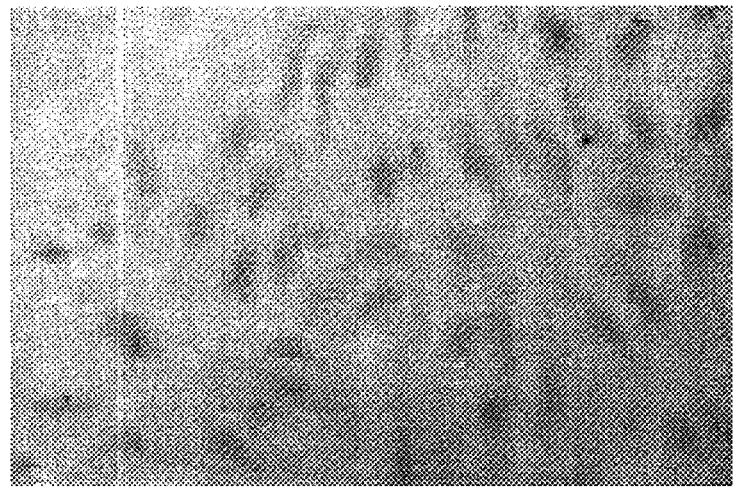
FIG. 27C shows that TNFα stimulation fails to produce translocation of NF-κB from cytoplasm to the nucleus in HUVECs pre-treated with 200 μg/mL ODS heparin.

FIG. 26 illustrates vasodilator responses to acetylcholine in isolated coronary rings from the ischemic-reperfused LAD, expressed as a percentage of U46619-induced precontraction. In the Control group, there is a statistically significant shift to the right in the concentration-response curve, representing reduced relaxation to acetylcholine. In contrast, the relaxant effect of coronary vessels to acetylcholine was preserved by HEP or ODS-HEP-treatment. Response curves are shown to incremental concentrations of acetylcholine (Ach) in the ischemic-reperfused left anterior descending (LAD) coronary artery precontracted with U46619. *$p<0.05$ HEP and ODS-HEP versus Control and *$p<0.05$ HEP versus Control.

The concentration of acetylcholine required to effect 50% relaxation ($EC_{50}$; -log [M]) was significantly greater for the Control (−6.98±0.06) compared to the HEP (−7.30±0.06) or ODSHEP (−7.20±0.05) groups (p<0.05). There were no differences in non-ischemic-reperfused ring preparations from LCx. In addition, there were no differences between LAD versus LCx vasodilator responses to incremental concentrations of A23187 (maximal relaxation=122±4 and 120±7% and EC50 log [M]=−7.18±0.06 and −7.17±0.09 for LAD and LCx, respectively) or sodium nitroprusside (maximal relaxation=129±5 and 121±4% and $EC_{50}$ log [M] =−7.31±0.02 and −7.29±0.04 for LAD and LCx, respectively), and responses were unaffected by HEP or ODS-HEP.

Example XII

2-O Desulfated Heparin Prevents Activation of Nuclear Factor-κB

This example shows that 2-O desulfated nonanticoagulant heparin prevents activation of nuclear factor-κB. This transcription factor, which regulates expression of a host of proinflammatory cytokines, is resident in the cytoplasm in unstimulated cells, but migrates to the nucleus when activated, there binding to its regulatory consensus sequence and fostering cytokine expression. NF-κB is held in the cytoplasmic compartment of cells by its inhibitor, I-κB, to which it is physically attached. NF-κB is cytosolic when complexed with its inhibitor, IκB, but is activated by phosphorylation, ubiquitination and proteolytic degration of IκB. Release from IκB exposes the NF-κB nuclear localization sequence (NLF), a highly cationic domain of eight amino acids (VQRDRQKLM, single-letter amino acid code) [SEQ ID NO:3] that targets nuclear translocation. NF-κB is activated in the heart by ischemia or ischemia and reperfusion (see Li C, et al., supra). Nuclear translocation of NF-κB is prevented by synthetic cell permeable peptides containing the NF-κB NLF, which competes for nuclear uptake (see Lin Y-Z, Yao S Y, Veach R A, Torgerson T R, Hawiger J, Inhibition of nuclear translocation of transcription factor NE-κB by a synthetic peptide containing a cell membrane-permeable motif and nuclear localization sequence. *J Biol Chem* 270:14255-14258, 1995). Heparin is readily bound and internalized into the cytosolic compartment by endothelium, vascular and airway smooth muscle, mesangial cells and even cardiac myocytes. Once internalized into the cytoplasm it is postulated that, the polyanion heparin might bind electrostatically to the positively charged amino acids of the NLF and prevent it from targeting NF-κB to the nuclear pore.

Figure 28:
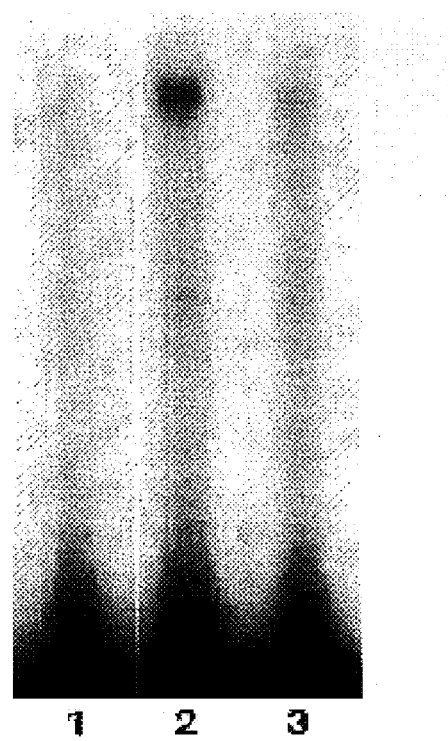
FIG. 28 are electrophoretic mobility shift assays of nuclear protein showing that ODS heparin decreases NF-κB DNA binding in TNF-stimulated HUVECs.

The increase in PMN adherence following ischemia-reperfusion is from enhanced expression of endothelial cell adhesion molecules, the transcription of which are strongly influenced by activation of the nuclear transcription factor NF-κB as a consequence of myocardial ischemia-reperfusion (see Li C, et al., supra). To study whether heparin could inhibit activation of NF-κB, immunohistochemical staining for NF-κB in human umbilical vein endothelial cells (HUVECs), with and without stimulation or pretreatment with ODS-HEP was performed. FIG. 28A shows that in the unstimulated state, nuclear factor-κ B (NF-κB, brown stained) is normally present only in the cytoplasm of HUVECs, but not in nuclei. In HUVECs stimulated with tumor necrosis factor α (TNFα) without addition of heparin, nuclei stain positive (brown) for the p65 component of NF-κB (FIG. 28B), corresponding to translocation of NF-κB from the cytoplasm to the nucleus. However, in HUVECs pre-treated with 200 μg/mL 2-O desulfated heparin, TNFα stimulation fails to produce translocation of NF-κB from cytoplasm to the nucleus (FIG. 28C).

Figure 29:
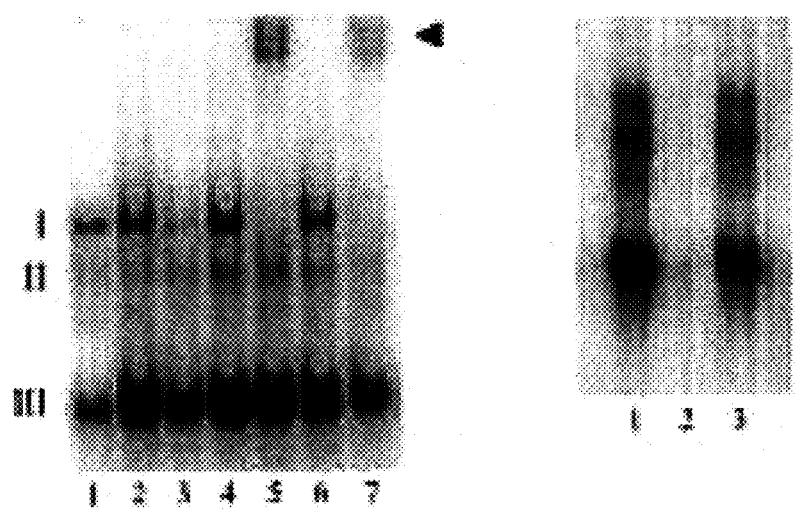
FIG. 29 are electrophoretic mobility shift assays of nuclear protein from ischemic-reperfused rat myocardium showing that ODS heparin decreases NF-κB DNA binding stimulated by ischemia-reperfusion.

Interruption of endothelial NF-κB activation by heparin and 2-O desulfated heparin was confirmed by electrophoretic mobility shift assays (EMSAs) as shown in FIG. 29. Tumor necrosis factor (TNF) stimulates endothelial DNA binding of NF-κB (FIG. 29, lane 2) compared to untreated controls (lane 1). Pretreatment with 200 μg/ml ODS-HEP eliminates NF-κB binding activity (lane 3), indicating that ODS-HEP prevents activation of NF-κB. HUECs were stimulated with 10 ng/ml TNFα for one hour and nuclear protein was harvested for electrophoretic mobility shift assays to detect binding of NF-κB, using the oligonucleotide consensus AFTTGAGGG-GACTTTCCCAGGC [SEQ ID NO 1], end-labeled with [$\gamma^{32}$P]ATP. Treatment of monolayers with TNF stimulates DNA binding of NF-κB (lane 2) compared to untreated controls (lane 1). Pretreatment of cells with 200 μg/ml ODS-HEP virtually eliminates NF-κB binding activity in nuclear protein extracts (lane 3), confirming that 2-O desulfated heparin prevents translocation of NF-κB from the cytoplasm to the nucleus.

2-O desulfated nonanticoagulant heparin also reduced DNA binding of NF-κB in ischemic-reperfused myocardium. Exposure of rat hearts to 15 minutes warm global ischemia and 15 minutes reperfusion increased DNA binding of myocardial nuclear protein to oligonucleotide sequences for NF-κB (FIG. 29A, lane 2). Three distinct bands of increased DNA binding were observed, all of which were eliminated by addition of excess unlabeled NF-κB oligonucleotide probe. Supershift experiments identified complex I as the band containing the p65 component of NF-κB (FIG. 29, lane 5). ODS-HEP treatment reduced ischemia-reperfusion related stimulation of NF-κB binding to DNA in all three bands (FIG. 29, lane 3). DNA binding of the p65-containing complex I was nearly eliminated by ODS-HEP, with a reduction of 54±6% as measured by densitometry in comparison to complex I of untreated ischemic-reperfused rat hearts (p<0.05, n=4). Thus, in addition to directly attenuating vascular adherence of PMNs to coronary endothelium, decreasing PMN accumulation in the area at risk and reducing myocardial necrosis, HEP or ODS-HEP also interrupt NF-κB activation and possibly adhesion molecule and myocardial cytokine expression.

Langendorf perfused rat hearts were subjected to 15 min warm global ischemia followed by 15 min reperfusion. Nuclear protein was then harvested for EMSAs to measure DNA binding of NF-κB. Compared to sham perfused control hearts (FIG. 29A, lane 1), ischemia and reperfusion typically increased DNA binding of myocardial nuclear protein to oligonucleotide sequences for NF-κB (lanes 2 and 4). Three distinct complexes were identified. Supershift experiments performed with antibody to p65 (lane 5), antibody to p50 (lane 6) or both antibodies (lane 7) demonstrated complex I to be shifted (arrow), identifying it as the band containing the p65 component of NF-κB. Pretreatment and perfusion with ODS-HEP (6 mg/kg iv 2 hours prior to heart perfusion; 100 μg/ml in perfusate) prevented the ischemia-reperfusion related stimulation of NF-κB DNA binding of the p65-containing complex I (lane 3). DNA binding of the p65-containing complex I was nearly eliminated by ODS-HEP, with a reduction of 54±6% as measured by densitometry in comparison to complex I of untreated ischemic-reperfused rat hearts (p<0.05, n=4). At right in FIG. 29B is shown a competition experiment in which nuclear proteins were incubated with 10× unlabeled NF-κB (lane 2) or cyclic AMP response element oligonucleotides (CRE, AGAGATTGCCTGACGTCA-GAGAGCTAG [SEQ ID NO 2], lane 3) for 5 minutes before addition of labeled NF-κB probe. Compared with binding reactions without excess probe (lane 1), addition of unlabeled NF-κB blocked DNA binding in all three complexes.

Example XIII

Reduction of Contractile Dysfunction Following Ischemia and Reperfusion of Isolated Rat Hearts by 2-O Desulfated Heparin This example shows that 2-O desulfated heparin reduces contractile dysfunction following ischemia and reperfusion of isolated rat hearts. After 15 minutes of both ischemia and reperfusion, hearts recovered high contractile function (95% of baseline, ischemia-reperfusion; and 93% of baseline ODS-HEP ischemia-reperfusion). Therefore, in additional studies, the period of ischemia was increased to 30 minutes. Both untreated and ODS-HEP treated hearts had reduced contractile function after 30 minutes of ischemia and 15 minutes of reperfusion (Pressure Rate Product=36,780±2,589 for Sham versus 4,575±1,856 for Ischemic-Reperfused hearts and 10,965±2,908 mm Hg/min for ODS-HEP treated Ischemic-Reperfused hearts, n=4 each), but hearts treated with ODS-HEP had significantly improved recovery of contractile function, which was 2.4 times better than that observed in hearts that did not receive ODS-HEP ($p<0.05$). Thus, in this severe model, ODS-HEP reduces both molecular and physiologic consequences of ischemia and reperfusion.

Heparin modified as taught herein to become 2-O desulfated heparin can provide these many anti-inflammatory benefits with the advantage of not causing the heparin-induced thrombocytopenia syndrome HIT-2 that is often accompanied by life-threatening thrombotic disease to the patient.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included, within the scope of the appended claims. Although specific terms are employed herein, they are used in a generic and descriptive sense only and not for purposes of limitation.

---

---

The invention claimed is:

1. A method for treating heparin-induced thrombocytopenia syndrome in a patient comprising administering to said patient an effective amount of a sulfated polysaccharide without inducing platelet activation or thrombosis in the presence of heparin- and platelet factor 4-complex reactive antibodies, wherein the sulfated polysaccharide comprises 2-O desulfated heparin or 2-O, 3-O desulfated heparin.

2. The method according to claim 1 wherein said sulfated polysaccharide has an average degree of sulfation of about 0.6 sulfate groups per monosaccharide or greater and an average molecular weight of 2.4 kD or greater.

3. The method according to claim 1 wherein said sulfated polysaccharide is a 2-O, 3-O desulfated heparin.

4. The method according to claim 1 wherein said administering is by a method selected from the group consisting of intravenously, subcutaneously, inhalation, orally, and rectally.

5. The method according to claim 1 wherein the 2-O desulfated heparin or 2-O, 3-O desulfated heparin is made by the process comprising alkalinizing a solution containing heparin to pH 13 or greater.

6. The method according to claim 1 wherein said effective amount is from 3 mg/kg to 100 mg/kg of sulfated polysaccharide.

7. A method for the amelioration of platelet activation caused by heparin with HIT antibodies in a patient comprising administering to said patient an effective amount of a sulfated polysaccharide without inducing platelet activation or thrombosis in the presence of heparin-and platelet factor 4-complex reactive antibodies, wherein the sulfated polvsaccharide comprises 2-O desulfated heparin or 2-O, 3-O desulfated hey arm.

8. The method according to claim 7 wherein said sulfated polysaccharide has an average degree of sulfation of about 0.6 sulfate groups per monosaccharide or greater and an average molecular weight of 2.4 kD or greater.

9. The method according to claim 7 wherein said sulfated polysaccharide is a 2-O, 3-O desulfated heparin.

10. The method according to claim 7 wherein said administrating is by a method selected from the group consisting of intravenously, subcutaneously, inhalation, orally, and rectally.

11. The method according to claim 7 wherein the 2-O desulfated heparin or 2-O, 3-O desulfated heparin is made by the process comprising alkalinizing a solution containing heparin to pH 13 or greater.

12. The method according to claim 7 wherein said effective amount is from 3 mg/kg to 100 mg/kg of sulfated polysaccharide.

13. A method for treating heparin-induced thrombocytopenia syndrome in a patient comprising administering to said patient an effective amount of a sulfated polysaccharide without inducing platelet activation or thrombosis in the presence of heparin- and platelet factor 4-complex reactive and administering a drug selected from the group consisting of anti-thrombin drugs, anti-platelet drugs, and anti-inflammatory drugs, wherein the sulfated polysaceharide comprises 2-O desulfated heparin or 2-O, 3-O desulfated heparin.

14. The method according to claim 13 wherein said sulfated polysaceharide has an average degree of sulfation of about 0.6 sulfate groups per monosaccharide or greater and an average molecular weight of 2.4 kD or greater.

15. The method according to claim 13 wherein said sulfated polysaccharide is a 2-O, 3-O desulfated heparin.

16. The method according to claim 13 wherein said administrating is by a method selected from the group consisting of intravenously, subcutaneously, inhalation, orally, and rectally.

17. The method according to claim 13 wherein the 2-O desulfated heparin or 2-O, 3-O desulfated heparin is made by the process comprising alkalinizing a solution containing heparin to pH 13 or greater.

18. The method according to claim 13 wherein said effective amount is from 3 mg/kg to 100 mg/kg of sulfated polysaccharide.

* * * * *

UNITED STATES PATENT AND TRADEMARK OFFICE
CERTIFICATE OF CORRECTION

PATENT NO. : 7,468,358 B2
APPLICATION NO. : 10/974566
DATED : December 23, 2008
INVENTOR(S) : Kennedy et al.

It is certified that error appears in the above-identified patent and that said Letters Patent is hereby corrected as shown below:

Column 13,
Line 63, "≧20%" should read --≥20%--.

Column 14,
Lines 19 and 23, "≧20%" should read --≥20%--.

Column 33,
Lines 9 and 10, "polvsaccharide" should read --polysaccharide--;
Line 11, "hey arm" should read --heparin--.

Column 34,
Lines 8 and 11, "polysaceharide" should read --polysaccharide--.

Signed and Sealed this

Second Day of June, 2009

JOHN DOLL
*Acting Director of the United States Patent and Trademark Office*

SEQUENCE LISTING

```
<160> NUMBER OF SEQ ID NOS: 3

<210> SEQ ID NO 1
<211> LENGTH: 22
<212> TYPE: DNA
<213> ORGANISM: Mus musculus

<400> SEQUENCE: 1
agttgagggg actttcccag gc                                             22

<210> SEQ ID NO 2
<211> LENGTH: 27
<212> TYPE: DNA
<213> ORGANISM: Rattus sp.

<400> SEQUENCE: 2
agagattgcc tgacgtcaga gagctag                                        27

<210> SEQ ID NO 3
<211> LENGTH: 9
<212> TYPE: PRT
<213> ORGANISM: Artificial Sequence
<220> FEATURE:
<223> OTHER INFORMATION: NF-kB nuclear localization sequence

<400> SEQUENCE: 3

Val Gln Arg Asp Arg Gln Lys Leu Met
 1               5
```